(12) United States Patent
Vanslyke et al.

(10) Patent No.: US 12,426,809 B2
(45) Date of Patent: Sep. 30, 2025

(54) SAFETY TOOLS FOR DECISION SUPPORT RECOMMENDATIONS MADE TO USERS OF CONTINUOUS GLUCOSE MONITORING SYSTEMS

(71) Applicant: DexCom, Inc., San Diego, CA (US)

(72) Inventors: Stephen J. Vanslyke, Carlsbad, CA (US); Naresh C. Bhavaraju, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 456 days.

(21) Appl. No.: 16/722,476

(22) Filed: Dec. 20, 2019

(65) Prior Publication Data

US 2020/0205704 A1 Jul. 2, 2020

Related U.S. Application Data

(60) Provisional application No. 62/786,089, filed on Dec. 28, 2018.

(51) Int. Cl.
*A61B 5/145* (2006.01)
*G16H 10/60* (2018.01)
(Continued)

(52) U.S. Cl.
CPC ......... *A61B 5/14532* (2013.01); *G16H 10/60* (2018.01); *G16H 20/17* (2018.01);
(Continued)

(58) Field of Classification Search
CPC ............ A61B 5/14532; A61B 2562/02; A61B 5/1495; A61B 5/0004; A61B 5/7275;
(Continued)

(56) References Cited

U.S. PATENT DOCUMENTS 5,626,140 A * 5/1997 Feldman ............... G06F 18/256
600/483
6,001,067 A 12/1999 Shults et al.
(Continued)

FOREIGN PATENT DOCUMENTS

CN 100553556 C * 10/2009 ............. G16H 40/67
CN 108961076 A * 12/2018 ............. G16H 50/30
(Continued)

OTHER PUBLICATIONS

Marling et al., "Toward Case-based Reasoning for Diabetes Management: A PreliminaryClinical Study and Decision Support System Prototype", Comp Intelligence (2009) 25(3):165-179.
(Continued)

*Primary Examiner* — Patrick Fernandes
(74) *Attorney, Agent, or Firm* — PATTERSON + SHERIDAN, LLP

(57) ABSTRACT

Systems and method are described for determining if a decision support recommendation is to be presented to a user for treatment of a diabetic state, including receiving a plurality of input data items impacting a diabetic state of a user of continuous glucose monitor, the input data items serving as input data to a process for determining a decision support recommendation; assigning a reliability level to each of the input data items; calculating a reliability metric based on the reliability levels assigned to each of the input data items; determining a decision support recommendation based on the process and the input data and presenting the decision support recommendation to the user on a user interface only if the reliability metric exceeds a threshold.

11 Claims, 8 Drawing Sheets

(51) Int. Cl.
*G16H 20/17* (2018.01)
*G16H 20/60* (2018.01)
*G16H 50/30* (2018.01)

(52) U.S. Cl.
CPC .............. *G16H 20/60* (2018.01); *G16H 50/30* (2018.01); *A61B 2562/02* (2013.01)

(58) Field of Classification Search
CPC ........ A61B 5/742; G16H 20/17; G16H 20/60; G16H 10/60; G16H 50/30; A61M 5/1723; A61M 2230/201
See application file for complete search history.

(56) References Cited

U.S. PATENT DOCUMENTS

| | | |
|---|---|---|
| 9,433,376 B2 | 9/2016 | Estes et al. |
| 9,480,401 B2 | 11/2016 | Koehler et al. |
| 10,004,435 B2 | 6/2018 | Larvenz et al. |
| 2004/0138540 A1* | 7/2004 | Baker, Jr. ............... A61B 5/145 600/336 |
| 2005/0157938 A1 | 7/2005 | Kondo et al. |
| 2006/0020187 A1 | 1/2006 | Brister et al. |
| 2006/0253296 A1 | 11/2006 | Liisberg et al. |
| 2007/0027385 A1 | 2/2007 | Brister et al. |
| 2008/0214902 A1* | 9/2008 | Lee .......................... A61B 5/16 600/301 |
| 2009/0137887 A1 | 5/2009 | Shariati et al. |
| 2009/0150812 A1* | 6/2009 | Baker ..................... G16H 40/63 715/764 |
| 2011/0027127 A1 | 2/2011 | Simpson et al. |
| 2012/0145152 A1 | 6/2012 | Lain et al. |
| 2012/0226124 A1 | 9/2012 | Blomquist |
| 2013/0150692 A1 | 6/2013 | Kamath et al. |
| 2014/0005508 A1 | 1/2014 | Estes et al. |
| 2014/0280341 A1 | 9/2014 | Rafei et al. |
| 2015/0118658 A1 | 4/2015 | Majou et al. |
| 2016/0081597 A1 | 3/2016 | Bhavaraju et al. |

FOREIGN PATENT DOCUMENTS

| | | | | |
|---|---|---|---|---|
| JP | 2007512588 A | | 5/2007 | |
| JP | 2017524221 A | | 8/2017 | |
| KR | 20160012758 A | * | 2/2016 | ............. G16H 50/30 |
| WO | 2005041103 A2 | | 5/2005 | |
| WO | WO-2009136243 A2 | * | 11/2009 | ............. G16H 20/17 |
| WO | 2016022761 A1 | | 2/2016 | |

OTHER PUBLICATIONS

International Search Report and Written Opinion dated Mar. 5, 2020 for Application No. PCT/US2019/067941.

Fletcher L., et al., "Feasibility of an Implanted, Closed-Loop, Blood-Glucose Control Device," Immunology 230, 2001, pp. 1-31.

* cited by examiner

SAFETY TOOLS FOR DECISION SUPPORT RECOMMENDATIONS MADE TO USERS OF CONTINUOUS GLUCOSE MONITORING SYSTEMS

INCORPORATION BY REFERENCE TO RELATED APPLICATION

Any and all priority claims identified in the Application Data Sheet, or any correction thereto, are hereby incorporated by reference under 37 CFR 1.57. This application claims priority to U.S. Provisional Patent Application No. 62/786,089, filed on Dec. 28, 2018. The aforementioned application is incorporated by reference herein in its entirety, and is hereby expressly made a part of this specification.

TECHNICAL FIELD

The present embodiments relate to continuous analyte monitoring, and, in particular, to signal analysis and result presentation of a continuous analyte monitoring system.

BACKGROUND

Diabetes mellitus is a disorder in which the pancreas cannot create sufficient insulin (Type I or insulin-dependent) and/or in which insulin is not effective (Type II or non-insulin-dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will become aware of a dangerous condition in time to counteract it, but it is also likely that he or she will not know whether his or her blood glucose value is going up (higher) or down (lower) based on conventional method. Diabetics thus may be inhibited from making educated insulin therapy decisions.

Another device that some diabetics used to monitor their blood glucose is a continuous analyte sensor, e.g., a continuous glucose monitor (CGM). A CGM typically includes a sensor that is placed invasively, minimally invasively or non-invasively. The sensor measures the concentration of a given analyte within the body, e.g., glucose, and generates a raw signal that is generated by electronics associated with the sensor. The raw signal is converted into an output value that is displayed on a display. The output value that results from the conversion of the raw signal is typically expressed in a form that provides the user with meaningful information, and in which form users become familiar with analyzing, such as blood glucose expressed in mg/dL.

SUMMARY

In a first aspect, method is provided for determining if a decision support recommendation is to be presented to a user for treatment of a diabetic state, comprising: identifying a current diabetic state of a user based at least in part on a glucose concentration level; receiving additional data that, along with the current diabetic state, serves as input data to a process for determining a decision support recommendation; assigning a reliability level to the additional data; calculating the decision support recommendation using the process and the input data; and presenting the decision support recommendation to the user on a user interface only if the assigned reliability level of the additional data exceeds a threshold.

In an embodiment of the first aspect or any other embodiment thereof, assigning the reliability level includes assigning a reliability level based at least in part on an identity of a source from which the additional data is obtained.

In an embodiment of the first aspect or any other embodiment thereof, the additional data includes an indication of food and drink ingested or to be ingested within a prescribed period of time.

In an embodiment of the first aspect or any other embodiment thereof, the indication includes data manually entered by the user.

In an embodiment of the first aspect or any other embodiment thereof, the indication includes nutritional data concerning the food or drink that is obtained from a third party.

In an embodiment of the first aspect or any other embodiment thereof, the nutritional data is automatically entered by an application.

In an embodiment of the first aspect or any other embodiment thereof, the nutritional data is automatically entered by scanning the nutritional information into the application.

In an embodiment of the first aspect or any other embodiment thereof, the additional data includes information describing past physiological response patterns of the user.

In an embodiment of the first aspect or any other embodiment thereof, the additional data includes an indication of a user activity level that has occurred or is to occur within a prescribed amount of time.

In an embodiment of the first aspect or any other embodiment thereof, assigning a reliability level includes assigning a higher reliability to additional information obtained through machine-to-machine communication than through manual entry-to-machine communication.

In an embodiment of the first aspect or any other embodiment thereof, the decision support recommendation includes a recommendation to ingest food or drink.

In an embodiment of the first aspect or any other embodiment thereof, the decision support recommendation includes a recommendation to inject a calculated amount of insulin.

In an embodiment of the first aspect or any other embodiment thereof, presenting the decision support recommendation includes determining when to present the decision recommendation based at least in part on the reliability level.

In an embodiment of the first aspect or any other embodiment thereof, receiving additional data includes receiving a plurality of additional data items of different types and assigning a reliability level to the additional data includes independently assigning a reliability level to each of the additional data items.

In an embodiment of the first aspect or any other embodiment thereof, presenting the decision support recommendation includes only presenting the decision support recommendation if a weighted average of the individual reliability levels exceeds a first threshold and if none of the individual reliability levels falls below a second threshold.

In an embodiment of the first aspect or any other embodiment thereof, the first and/or second thresholds are selected based at least in part on a type of decision support recommendation that is calculated.

In an embodiment of the first aspect or any other embodiment thereof, the threshold is selected based at least in part on a type of decision support recommendation that is determined.

In an embodiment of the first aspect or any other embodiment thereof, presenting the decision support recommendation includes presenting a more conservative support recommendation that promotes patient safety when the assigned reliability level is within a range specified by upper and lower thresholds.

In an embodiment of the first aspect or any other embodiment thereof, the calculated amount of insulin is calculated as a part of the process for determining the decision support recommendation.

In an embodiment of the first aspect or any other embodiment thereof, assigning a reliability level to the additional data includes assigning a reliability level to the additional data using machine-learning techniques.

In an embodiment of the first aspect or any other embodiment thereof, the glucose concentration level is obtained from a glucose sensor in a continuous glucose monitor.\

In an embodiment of the first aspect or any other embodiment thereof, identifying the current diabetic state of the user includes receiving sensor data from a glucose sensor associated with a continuous glucose monitor.

In an embodiment of the first aspect or any other embodiment thereof, the user interface is incorporated in a display device that receives the sensor data from the glucose sensor.

In an embodiment of the first aspect or any other embodiment thereof, the display device receives the sensor data from the glucose sensor over a wireless communication link.

In an embodiment of the first aspect or any other embodiment thereof, presenting the decision support recommendation to the user on a user interface includes presenting the decision support recommendation to the user on the user interface of the display device.

In an embodiment of the first aspect or any other embodiment thereof, a continuous glucose sensor application residing on the display device receives the sensor data and causes the decision support recommendation to be presented to the user on the user interface.

In a second aspect, a method is provided for determining if a decision support recommendation is to be calculated, comprising: identifying a current diabetic state of a user based at least in part on a glucose concentration level; receiving additional data that, along with the current diabetic state, serves as input data to a process for determining a decision support recommendation; assigning a reliability level to the additional data; and calculating the decision support recommendation using the process and the input data only if the assigned reliability level of the additional data exceeds a threshold.

In an embodiment of the second aspect or any other embodiment thereof, assigning the reliability level includes assigning a reliability level based at least in part on an identity of a source from which the additional data is obtained.

In an embodiment of the second aspect or any other embodiment thereof, the additional data includes an indication of food and drink ingested or to be ingested within a prescribed period of time.

In an embodiment of the second aspect or any other embodiment thereof, the indication includes data manually entered by the user.

In an embodiment of the second aspect or any other embodiment thereof, the indication includes nutritional data concerning the food or drink that is obtained from a third party.

In an embodiment of the second aspect or any other embodiment thereof, wherein the nutritional data is automatically entered by an application.

In an embodiment of the second aspect or any other embodiment thereof, the nutritional data is automatically entered by scanning the nutritional information into the application.

In an embodiment of the second aspect or any other embodiment thereof, the additional data includes information describing past physiological response patterns of the user.

In an embodiment of the second aspect or any other embodiment thereof, the additional data includes an indication of a user activity level that has occurred or is to occur within a prescribed amount of time.

In an embodiment of the second aspect or any other embodiment thereof, assigning a reliability level includes assigning a higher reliability to additional information obtained through machine-to-machine communication than through manual entry-to-machine communication.

In an embodiment of the second aspect or any other embodiment thereof, the decision support recommendation includes a recommendation to ingest food or drink.

In an embodiment of the second aspect or any other embodiment thereof, the decision support recommendation includes a recommendation to inject a calculated amount of insulin.

In an embodiment of the second aspect or any other embodiment thereof, receiving additional data includes receiving a plurality of additional data items of different types and assigning a reliability level to the additional data includes independently assigning a reliability level to each of the additional data items.

In an embodiment of the second aspect or any other embodiment thereof, calculating the decision support recommendation includes only calculating the decision support recommendation if a weighted average of the individual reliability levels exceeds a first threshold and if none of the individual reliability levels falls below a second threshold.

In an embodiment of the second aspect or any other embodiment thereof, the threshold is selected based at least in part on a type of decision support recommendation that is determined.

In an embodiment of the second aspect or any other embodiment thereof, the calculated amount of insulin is calculated as a part of the process for determining the decision support recommendation.

In a third aspect, a method is provided for determining if a decision support recommendation is to be presented to a user for treatment of a diabetic state, comprising: receiving a plurality of input data items impacting a diabetic state of a user of continuous glucose monitor, the input data items serving as input data to a process for determining a decision support recommendation; assigning a reliability level to each of the input data items; calculating a reliability metric based on the reliability levels assigned to each of the input data items; determining a decision support recommendation based on the process and the input data and presenting the decision support recommendation to the user on a user interface only if the reliability metric exceeds a threshold.

In an embodiment of the third aspect or any other embodiment thereof, calculating the reliability metric includes calculating the reliability metric based on an average of the reliability levels of the each of the input data items In an embodiment of the third aspect or any other embodiment thereof, the average of the reliability levels is a weighted average.

In an embodiment of the third aspect or any other embodiment thereof, the plurality of input data items includes sensor data from a glucose sensor in the continuous glucose monitor.

In an embodiment of the third aspect or any other embodiment thereof, assigning a reliability level includes assigning a reliability level to the sensor data based on one more factors selected from the group comprising: signal quality, sensor calibration, connectivity, glucose sensor age and expected lifetime of the glucose sensor.

In an embodiment of the third aspect or any other embodiment thereof, determining and presenting the decision support recommendation includes determining the decision support recommendation even if the reliability metric does not exceed the threshold while presenting the decision support recommendation to the user on the user interface only if the reliability metric exceeds the threshold.

In an embodiment of the third aspect or any other embodiment thereof, determining and presenting the decision support recommendation includes determining the decision support recommendation only if the reliability metric exceeds the threshold and presenting the decision support recommendation to the user only if the reliability metric exceeds the threshold.

In an embodiment of the third aspect or any other embodiment thereof, assigning a reliability level to each of the input data items includes assigning a reliability level to at least one of the input data items based on uncertainty in an accuracy of a value of the at least one input data items.

In an embodiment of the third aspect or any other embodiment thereof, assigning a reliability level to each of the input data items includes assigning a reliability level to at least one of the input data items based on a degree of uncertainty of an impact of the at least one input data item on the diabetic state of the user.

In an embodiment of the third aspect or any other embodiment thereof, assigning the reliability level includes assigning a reliability level based at least in part on an identity of a source from which the additional data is obtained.

In an embodiment of the third aspect or any other embodiment thereof, the additional data includes an indication of food and drink ingested or to be ingested within a prescribed period of time.

In an embodiment of the third aspect or any other embodiment thereof, the indication includes data manually entered by the user.

In an embodiment of the third aspect or any other embodiment thereof, the indication includes nutritional data concerning the food or drink that is obtained from a third party.

In an embodiment of the third aspect or any other embodiment thereof, the nutritional data is automatically entered by an application.

In an embodiment of the third aspect or any other embodiment thereof, the nutritional data is automatically entered by scanning the nutritional information into the application.

In an embodiment of the third aspect or any other embodiment thereof, the additional data includes information describing past physiological response patterns of the user.

In an embodiment of the third aspect or any other embodiment thereof, the additional data includes an indication of a user activity level that has occurred or is to occur within a prescribed amount of time.

In an embodiment of the third aspect or any other embodiment thereof, assigning a reliability level includes assigning a higher reliability to additional information obtained through machine-to-machine communication than through manual entry-to-machine communication.

In an embodiment of the third aspect or any other embodiment thereof, the decision support recommendation includes a recommendation to ingest food or drink.

In an embodiment of the third aspect or any other embodiment thereof, the decision support recommendation includes a recommendation to inject a calculated amount of insulin.

In an embodiment of the third aspect or any other embodiment thereof, presenting the decision support recommendation only if the assigned reliability of the additional data exceeds a threshold further includes determining when to present the decision recommendation based at least in part on the reliability level.

In an embodiment of the third aspect or any other embodiment thereof, presenting the decision support recommendation includes only presenting the decision support recommendation if a weighted average of the individual reliability levels exceeds a first threshold and if none of the individual reliability levels falls below a second threshold.

In an embodiment of the third aspect or any other embodiment thereof, the threshold is selected based at least in part on a type of decision support recommendation that is calculated.

In an embodiment of the third aspect or any other embodiment thereof, assigning a higher threshold to a decision support recommendation that is therapeutic than a decision support recommendation that adjunctive.

In an embodiment of the third aspect or any other embodiment thereof, the threshold is selected based at least in part on a type of decision support recommendation that is determined.

In an embodiment of the third aspect or any other embodiment thereof, presenting the decision support recommendation includes presenting a more conservative support recommendation that promotes patient safety when the assigned reliability level is within a range specified by upper and lower thresholds.

In an embodiment of the third aspect or any other embodiment thereof, the plurality of input data items includes an indication of food and drink ingested or to be ingested within a prescribed period of time.

In an embodiment of the third aspect or any other embodiment thereof, assigning a reliability level includes assigning a lower reliability level to the input data item obtained from the indication of food and drink when the indication includes data manually entered by the user relative and assigning a higher reliability level to the input data item obtained from the indication of food and drink when the indication includes nutritional data concerning the food and drink that is obtained from a third party or nutritional data that is automatically entered by an application.

In an embodiment of the third aspect or any other embodiment thereof, assigning a reliability level to the input data items includes assigning a reliability level to the input data items using machine-learning techniques.

In an embodiment of the third aspect or any other embodiment thereof, the glucose concentration level is obtained from a glucose sensor in a continuous glucose monitor.

In an embodiment of the third aspect or any other embodiment thereof, the user interface is incorporated in a display device that receives the sensor data from the glucose sensor.

In an embodiment of the third aspect or any other embodiment thereof, the display device receives the sensor data from the glucose sensor over a wireless communication link.

In an embodiment of the third aspect or any other embodiment thereof, presenting the decision support recommendation to the user on a user interface includes presenting the decision support recommendation to the user on the user interface of the display device.

In an embodiment of the third aspect or any other embodiment thereof, a continuous glucose sensor application residing on the display device receives the sensor data and causes the decision support recommendation to be presented to the user on the user interface.

In a fourth aspect, a system for providing decision support recommendations concerning a diabetic state of a user, comprising: a continuous glucose monitor (CGM) application running on a mobile device, the CGM application being configured to receive data from a glucose sensor on at least a periodic or occasional basis and to display glucose calibration data; a decision support recommendation application running as a subroutine within the CGM application or running as a parallel process within the CGM application on the mobile device and receiving data from the CGM application, the decision support recommendation application configured to perform a method set forth in an embodiment of the first, second or third aspects or any other embodiments thereof,

DETAILED DESCRIPTION

Figure 1:
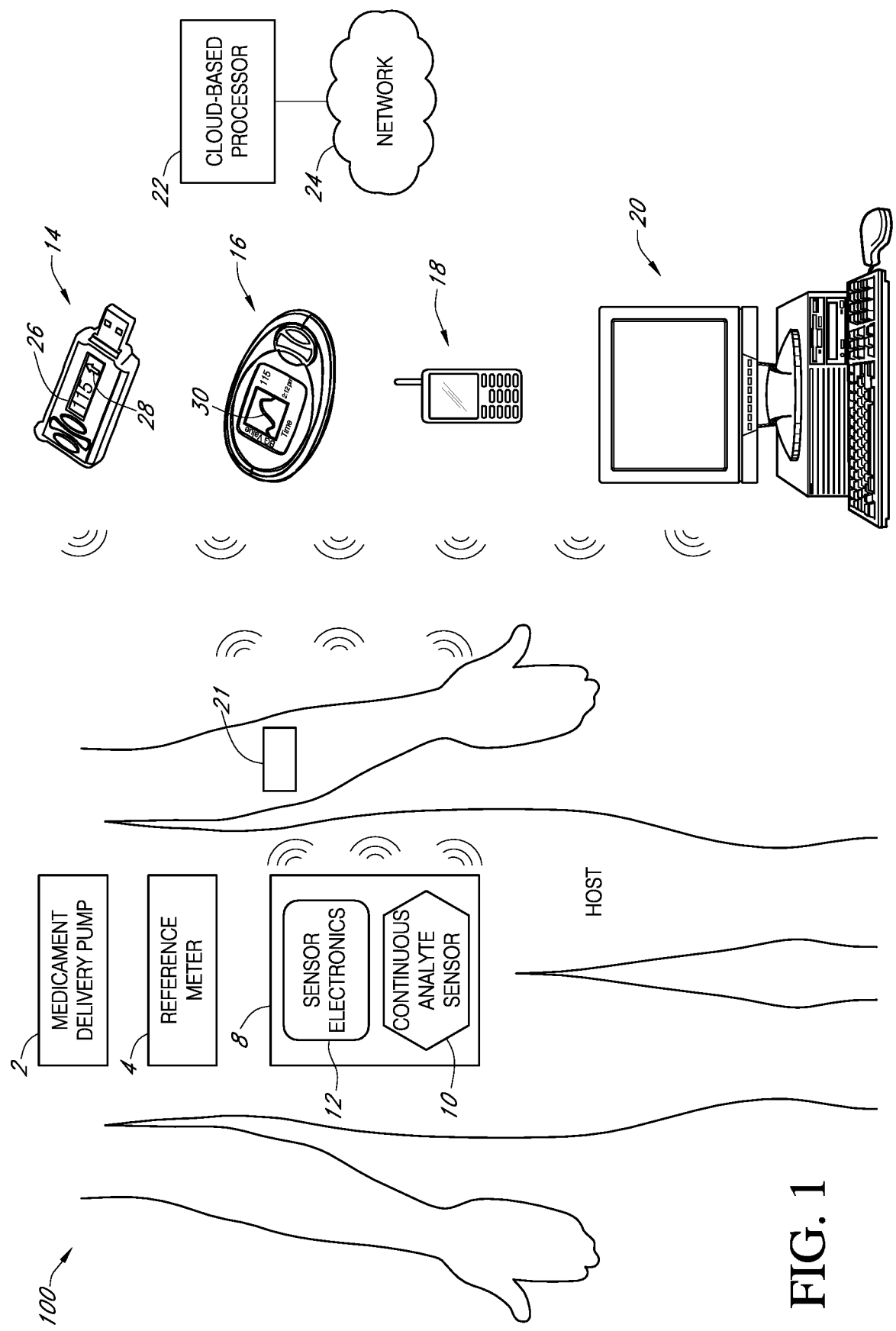
FIG. 1 is a block diagram of an integrated system of the preferred embodiments, including a continuous glucose sensor and a medicament delivery device.

Continuous glucose monitoring (CGM) systems that display the current glucose levels provide the user with continuous information about their current metabolic status and, therefore, additionally with continuous indicator information about the trend in glucose level changes. This information facilitates the countless therapeutic decisions that users with diabetes need to make in relation to food intake, exercise, and insulin delivery.

Even for users whose therapy does not include the use of insulin, monitoring can help show the effects of food choices, physical activity, medicines, and stress-management efforts. Monitoring at different times on different days (as opposed to monitoring at the same times every day) provides valuable information about blood glucose levels over the course of the day. It also allows patterns in blood glucose levels to be observed, such as highs or lows at particular times of day and/or related to certain events.

Users can achieve improved metabolic control and a reduced risk of acute metabolic deteriorations through personalized and flexible adaptation of their therapy in response to their current glucose levels and the trends in changes in their glucose levels. This information allows users to determine, for example, if they are at risk of a hypoglycemic event, if the insulin dose selected was appropriate for the current meal and if physical activity needs to be compensated for with, e.g., the intake of additional carbohydrates. That is, CGM systems provide immediate, ongoing feedback that the user can apply towards reaching desired goals.

CGM systems permit retrospective analysis of large quantities of data, allowing the user and their healthcare team to generate statistics and detect patterns/trends that facilitate therapeutic adjustments. This analysis allows a variety of graphs and statistics to be generated, including for instance, the glucose average, standard deviation, percent of time spent above, below and within target range, number of excursions above and below target range, detailed daily reports, and modal day reports which superimpose multiple days of trend data onto a single chart. Among other things, this analysis allows alarms to be generated warning the user of pending high or low glucose levels.

In addition to measurements of blood glucose levels, a retrospective analysis will also generally require external information that is not directly obtained from the analyte sensor in the CGM system. The external data may correspond, e.g., to past or present user indications of how the user feels, what the user ate, the amount of user activity, and so on. The external data, which may be user-entered data, derived data, or data obtained from other applications or sensors or other sources, may also constitute numerous other parameters, as will be described below.

The analysis of the large amount historical information obtained by CGM systems can provide an understanding of patterns that allow even better metabolic control than is possible from simply being aware of current glucose levels and the trends in changing glucose levels. For instance, viewing CGM data after meals, especially for the first one to two hours, can reveal both the timing and magnitude of postprandial spikes. Users and clinicians can evaluate the postprandial effects of different food types for meal planning purposes, determining the optimal timing of mealtime boluses and/or the need for mealtime rapid-acting insulin. As another example, analyzing glucose levels three to four hours post-bolus can provide useful insight regarding bolus dosing. Glucose levels that are consistently above or below target at this time may indicate a need to adjust meal doses (insulin-to-carbohydrate ratios) or correction doses (insulin sensitivity). As yet a further example, for those using an incretin to regulate glucose levels, a review of post-meal patterns should indicate whether a sufficient dose is being taken, as glucose levels should remain fairly stable post-meal. For those taking rapid-acting insulin along with an incretin, insulin dose timing can be evaluated. A glucose drop soon after eating, followed by a rise over the next couple of hours, may indicate a need to either delay or extend delivery of the mealtime insulin.

The analysis of historical information can also be used to provide a better understanding of the extent to which exercise, and different forms of exercise, contribute to short-term and long-term glucose patterns. Likewise, the impact of stress and illness on glucose control can also be analyzed.

Evaluating all the available analytical data, including both the glucose levels and trends as well as the external data, and using it to provide guidance to the user concerning the user's daily routines to improve disease management and to identify the need for therapeutic interventions on a timely basis can be a difficult task for the clinician, let alone for the user. To address this issue, CGM systems may be equipped with decision support functionality, which uses analyte sensor data and/or other data, e.g., external data, as inputs to an algorithm to provide a user prompt on a display and/or a command to a mechanical device such as a medicament, e.g., insulin, pump. The user prompt may include a treatment recommendation for therapeutic interventions such as eating a snack, exercising or taking an appropriate medication. It should be noted that decision support recommendations may include recommendations that are provided for non-adjunctive use of CGM systems for treatment decisions that do not require self-monitoring of blood glucose (SMBG).

Instead of presenting a specific treatment recommendation, in some cases decision support recommendations may include general guidelines to facilitate and encourage healthy behavior on the part of the user. For instance, some decision support recommendations may encourage the user to check glucose levels often or to learn what factors make the user's glucose levels go up or down. Likewise, other decision support recommendations may encourage the user to eat healthy, participate in physical activity, such as walking after meals, or take medication as directed. Some types of decision support recommendations may serve as reminders, such as reminding the user that carbohydrates increase glucose levels. Yet other types of decision support recommendations may be informational in nature, such as providing the user with information allowing them to quickly and easily determine food serving sizes. For instance, such a decision support recommendation may indicate that a single serving of meat is approximately equal to a deck of cards and that a single serving of fruit or vegetables is approximately the size of a baseball. As another example, such informational decision support recommendations may identity particular foods that are high or low carbohydrates foods or high or low glycemic index foods.

As decision support algorithms become more commonly employed in CGM systems, safety concerns become an important issue. It is essential that any treatment recommendations provided to the user by decision support algorithms only promote improved health and safety while any treatment recommendations that could result in medical complications are avoided. In some cases this may require providing a more conservative or protective recommendation to ensure user safety than would be typically be provided by a clinician given the same analytical data.

One factor that may be used to determine whether a particular decision support recommendation is sufficiently safe to be presented to the user by the CGM system is the reliability of the input data (e.g., the analyte sensor data and the external data) that is used to generate the decision support recommendation. As explained in more detail below, a reliability rating or level may be assigned to each individual input data item that is used to generate the recommendation. The reliability rating or level may be determined based on a variety of factors such as the source of the input data item (e.g. data manually entered by the user versus sensor data), the precision of the data (e.g., whether nutritional data concerning a meal or a level of physical activity is provided in qualitative or quantitative terms), and so on.

Illustrative Continuous Glucose Monitoring System

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor capable of measuring the concentration of glucose in a host, the systems and methods of embodiments can be applied to any measurable analyte. Some exemplary embodiments described below utilize an implantable glucose sensor. However, it should be understood that the devices and methods described herein can be applied to any device capable of detecting a concentration of analyte and providing an output signal that represents the concentration of the analyte.

As noted, in some embodiments, the analyte sensor is an implantable glucose sensor, such as described with reference to U.S. Pat. No. 6,001,067 and U.S. Patent Publication No. US-2011-0027127-A1. In some embodiments, the analyte sensor is a transcutaneous glucose sensor, such as described with reference to U.S. Patent Publication No. US-2006-0020187-A1. In yet other embodiments, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1. These patents and publications are incorporated herein by reference in their entirety.

The following description and examples described the present embodiments with reference to the drawings. In the drawings, reference numbers label elements of the present embodiments. These reference numbers are reproduced below in connection with the discussion of the corresponding drawing features.

FIG. 1 is a block diagram of an integrated system of the preferred embodiments, including a continuous glucose sensor and a medicament delivery device. Such is an exemplary environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate from sensor electronics module 12, but electronically coupled via inductive coupling or the like. Further, the sensor electronics module 12, medicament delivery pump 2, and/or analyte reference meter 4, may communicate with one or more additional devices, such as any or all of display devices 14, 16, 18, and/or 20. The display devices 14, 16, 18, and 20 generally include a processor, memory, storage, and other components sufficient to run an application including a decision support module.

In some implementations, the system 100 of FIG. 1 may also include a cloud-based processor 22 configured to analyze analyte data, medicament delivery data and/or other user-related data provided over network 24 directly or indirectly from one or more of sensor system 8, medicament delivery pump 2, reference analyte meter 4, and display devices 14, 16, 18, 20. Based on the received data, the processor 22 can further process the data, generate reports providing statistics based on the processed data, trigger notifications to electronic devices associated with the host or caretaker of the host, or provide processed information to any of the other devices of FIG. 1. In some exemplary implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

In some exemplary implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well, such as by the devices 14, 16, 18, and/or 20. The sensor electronics module 12 may include hardware, firmware, software, or a combination thereof, to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, and 20. The display devices 14, 16, 18, and/or 20 may be configured for processing and presenting information, such sensor information transmitted by the sensor electronics module 12 for display at the display device. The display devices 14, 16, 18, and 20 can also trigger alarms and/or provide decision support recommendations based on the analyte sensor data.

In FIG. 1, display device 14 is a key fob-like display device, display device 16 is a hand-held application-specific computing device 16 (e.g., the DexCom G4™ Platinum receiver commercially available from DexCom, Inc.), display device 18 is a general purpose smart phone or tablet computing device 20 (e.g., a phone running the Android™ OS, an Apple™ iPhone™, iPad™, or iPod Touch™. commercially available from Apple, Inc.), and display device 20 is a computer workstation 20. In some exemplary implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the display device 18) and may be configured to display a limited set of displayable sensor information, such as a numerical value 26 and an arrow 28. Some systems may also include a wearable device 21, such as described in U.S. Provisional Patent Application No. 61/904,341, filed Nov. 14, 2013, and entitled "Devices and Methods for Continuous Analyte Monitoring" and U.S. Pat. No. 10,004, 435 claiming priority to same, the entire disclosures of which are hereby expressly incorporated by reference in their entireties. The wearable device 21 may include any device(s) that is/are worn on, or integrated into, a user's vision, clothes, and/or bodies. Example devices include wearable devices, anklets, glasses, rings, necklaces, arm bands, pendants, belt clips, hair clips/ties, pins, cufflinks, tattoos, stickers, socks, sleeves, gloves, garments (e.g. shirts, pants, underwear, bra, etc.), "clothing jewelry" such as zipper pulls, buttons, watches, shoes, contact lenses, subcutaneous implants, eyeglasses, cochlear implants, shoe inserts, braces (mouth), braces (body), medical wrappings, sports bands (wrist band, headband), hats, bandages, hair weaves, nail polish, artificial joints/body parts, orthopedic pins/devices, implantable cardiac or neurological devices, etc. The small display device 14 and/or the wearable device 21 may include a relatively small display (e.g., smaller than the display device 18) and may be configured to display graphical and/or numerical representations of sensor information, such as a numerical value 26 and/or an arrow 28. In contrast, display devices 16, 18 and 20 can be larger display devices that can be capable of displaying a larger set of displayable information, such as a trend graph 30 depicted on the hand-held receiver 16 in addition to other information such as a numerical value and arrow.

It is understood that any other user equipment (e.g., computing devices) configured to at least present information (e.g., a medicament delivery information, discrete self-monitoring analyte readings, heart rate monitor, caloric intake monitor, and the like) can be used in addition to or instead of those discussed with reference to FIG. 1.

In some exemplary implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations of FIG. 1, the continuous analyte sensor 10 may comprise a glucose sensor configured to measure glucose in the blood using one or more measurement techniques, such as enzymatic, chemical, physical, electrochemical, fluorescent, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide data, such as a data stream, indicative of the concentration of glucose in a host. The data stream may be a raw data signal, which is converted into a calibrated and/or filtered data stream used to provide a value of glucose to a host, such as a user, a patient, or a caregiver (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, intraocular, or an intravascular sensor.

In some implementations of FIG. 1, the continuous analyte sensor system 8 includes a Dexcom G4™ Platinum glucose sensor and transmitter commercially available from Dexcom, Inc., or at such sensor systems, for continuously monitoring a host's glucose levels.

Figure 2:
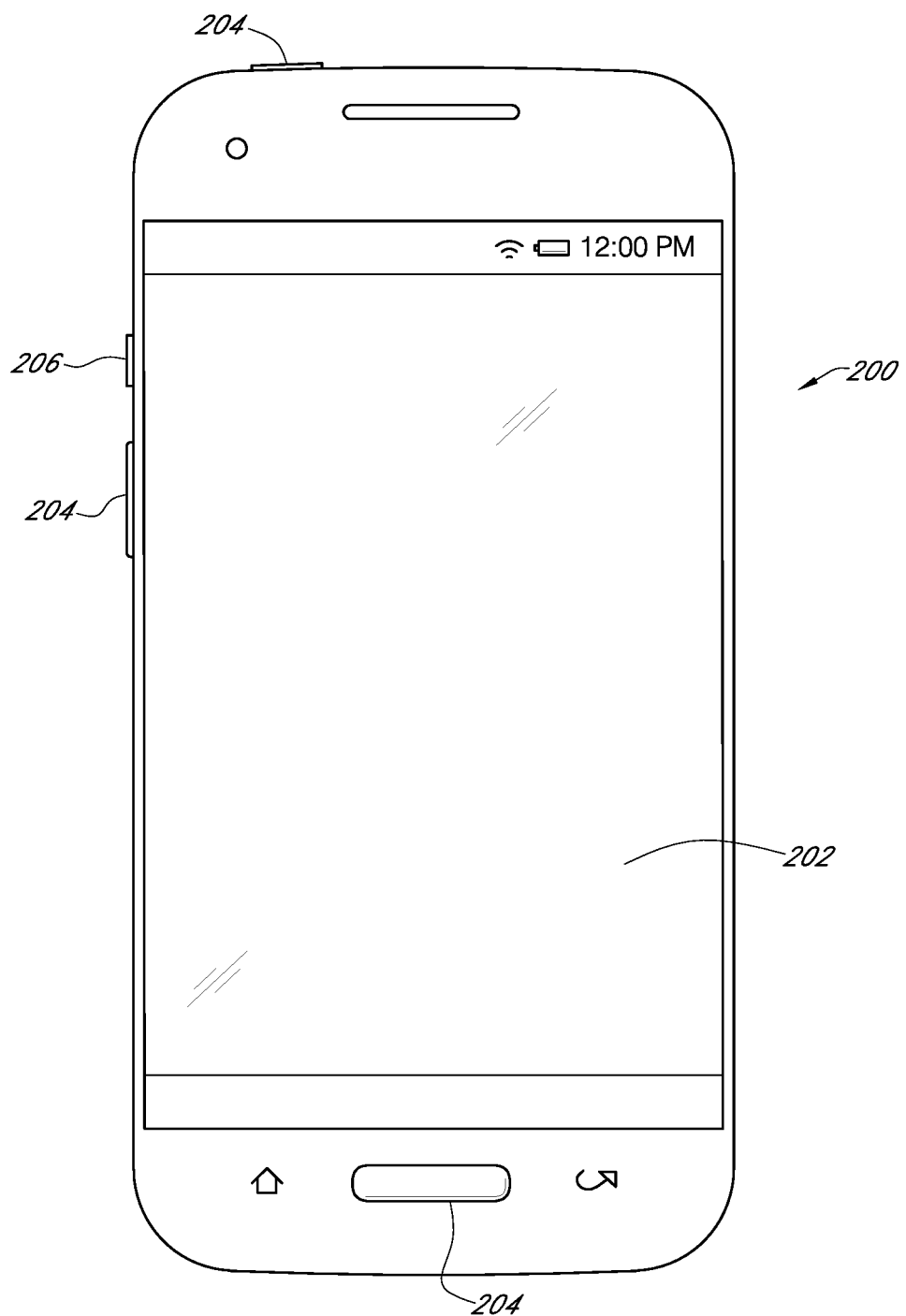
FIG. 2 is a front elevation view of an electronic device configured for use with the present systems and methods.

FIG. 2 illustrates one embodiment of an electronic device 200 configured for use with the present systems and methods. The electronic device 200 includes a display 202 and one or more input/output (I/O) devices, such as one or more buttons 204 and/or switches 206, which when activated or clicked perform one or more functions. In some embodiments the electronic device 200 may be mobile communication device. For instance, in the illustrated embodiment, the electronic device 200 is a smartphone, and the display 202 comprises a touchscreen, which also functions as an I/O device. In other embodiments, the electronic device 200 may comprise a device or devices other than a smartphone, such as a receiver of a CGM system, a smartwatch, a tablet computer, a mini-tablet computer, a handheld personal digital assistant (PDA), a game console, a multimedia player, a wearable device, such as those described above, a screen in an automobile or other vehicle, etc. While the electronic device 200 is illustrated as a smartphone in the figures, the electronic device 200 can be any of the other electronic devices mentioned herein and/or incorporate the functionality of any or all of the other electronic devices, including wherein some or all of the functionally is embodied on a remote server.

Figure 3:
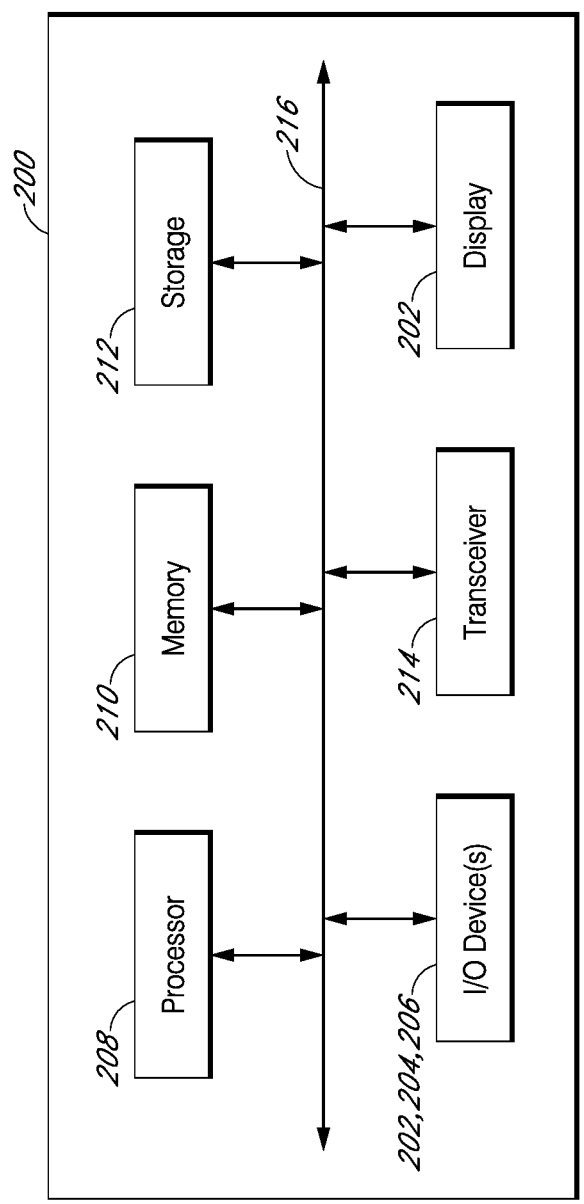
FIG. 3 is a functional block diagram of the electronic device of FIG. 1.

FIG. 3 is a block diagram of the electronic device 200 shown in FIG. 2, illustrating its functional components in accordance with some embodiments. The electronic device 200 includes the display 202 and one or more input/output ("I/O") device(s) 204, 206, as described above with respect to FIG. 2. The display 202 may be any device capable of displaying output, such as an LCD or LED screen and others. The input/output (I/O) devices 202, 204, 206 may comprise, for example, a keyboard (not shown), one or more buttons 204, one or more switches 206, etc. In embodiments including a touchscreen, the display 202 also functions as an I/O device.

The electronic device 200 further includes a processor 208 (also referred to as a central processing unit (CPU)), a memory 210, a storage device 212, a transceiver 214, and may include other components or devices (not shown). The memory 210 is coupled to the processor 208 via a system bus or a local memory bus 216. The processor 208 may be, or may include, one or more programmable general-purpose or special-purpose microprocessors, digital signal processors (DSPs), programmable controllers, application specific integrated circuits (ASICs), programmable logic devices (PLDs), or the like, or a combination of such hardware-based devices.

The memory 210 provides the processor 208 access to data and program information that is stored in the memory 210 at execution time. Typically, the memory 210 includes random access memory (RAM) circuits, read-only memory (ROM), flash memory, or the like, or a combination of such devices.

The storage device 212 may comprise one or more internal and/or external mass storage devices, which may be or may include any conventional medium for storing large volumes of data in a non-volatile manner. For example, the storage device 212 may include conventional magnetic disks, optical disks, magneto-optical (MO) storage, flash-based storage devices, or any other type of non-volatile storage devices suitable for storing structured or unstructured data. The storage device 212 may also comprise storage in the "cloud" using so-called cloud computing. Cloud computing pertains to computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction.

The electronic device 200 may perform various processes, such as, for example, correlating data, pattern analysis, and other processes. In some embodiments, the electronic device 200 may perform such processes on its own. Alternatively, such processes may be performed by one or more other devices, such as one or more cloud-based processors 22 described above. In still further embodiments, these processes may be performed in part by the electronic device 200 and in part by other devices. Various example processes are described herein with reference to the electronic device 200. It should be understood that these example processes are not limited to being performed by the electronic device 200 alone. Further, as used herein, the term "electronic device" should be construed to include other devices with which the electronic device 200 interacts, such as one or more cloud-based processors, servers, etc.

The electronic device 200 may also include other devices/interfaces for performing various functions. For example, the electronic device 200 may include a camera (not shown).

The transceiver 214 enables the electronic device 200 to communicate with other computing systems, storage devices, and other devices via a network. While the illustrated embodiment includes a transceiver 214, in alternative embodiments a separate transmitter and a separate receiver may be substituted for the transceiver 214.

In some embodiments, the processor 208 may execute various applications, for example, a CGM application, which may be downloaded to the electronic device 200 over the Internet and/or a cellular network, and the like. Data for various applications may be shared between the electronic device 200 and one or more other devices/systems, and stored by storage 212 and/or on one or more other devices/systems. This CGM application may include a decision support module and/or may include processing sufficient to operate decision support assessment functions and methods as described below.

In certain of the present embodiments, the sensor 10 of the continuous analyte sensor system 8 of FIG. 1 is inserted into the skin of a host. A new sensor session is then initiated with the sensor 10, the sensor electronics 12, and the electronic device 200. Numerous techniques may be employed for initializing the sensor 10. For example, initialization may be triggered when the sensor electronics 12 engages the sensor 10. In another example, initialization may be triggered by a mechanical switch, such as a switch (not shown) on a snap-in base that receives the sensor electronics 12. When the sensor electronics 12 are snapped into the base, the switch is automatically tripped. In another example, initialization may be menu driven, and the user may be prompted by a user interface on the display 202 of the electronic device 200 to begin initialization by making a selection on the user interface, such as by pushing a button or touching a designated area on a display 202 (which may comprise a touchscreen). In another example involving a non-invasive sensor that is applied to the wearer's skin, the sensor 10 may sense when it is in contact with skin and start automatically. Further, the analyte sensor system 8 can detect use of a new sensor 10 using any of the above techniques, automatically prompt the user to confirm the new sensor session by way of a prompt on a user interface of the system 8, and initiate an initialization response to the user confirmation responsive to the prompt. Additional examples of initializing the sensor 10 are found in U.S. patent application Ser. No. 13/796,185, filed on Mar. 12, 2013, and corresponding to U.S. Pat. No. 9,433,376, the entire disclosures of which are hereby incorporated by reference herein.

Figure 4:
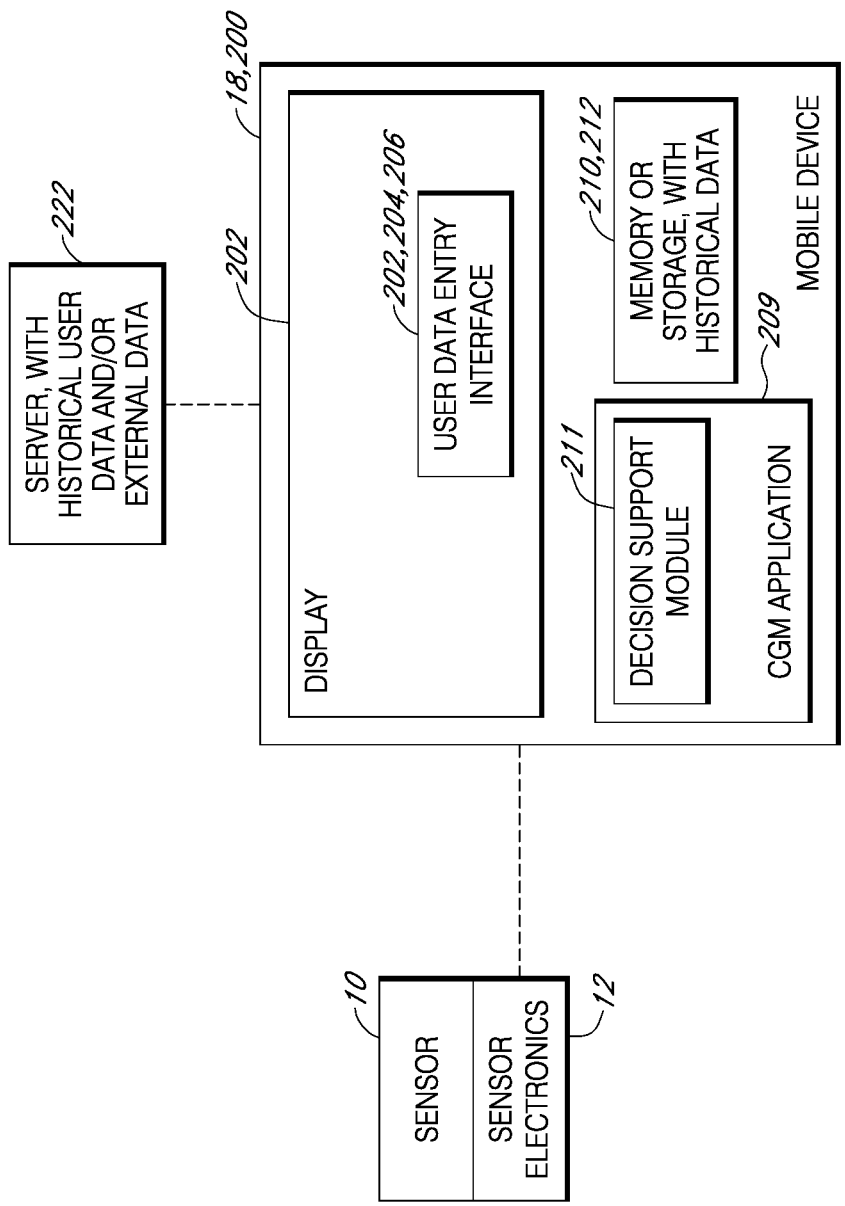
FIG. 4 depicts a logical diagram of certain components of the system of FIG. 1.

FIG. 4 illustrates an exemplary logical diagram for the continuous analyte monitoring system 100, illustrating in particular components involved in determination of sensor results and portrayal of calculations and determinations of decision support recommendations based on the results as well as on other factors. In particular, measurements from the sensor 10 are processed by the sensor electronics 12 and sent to the mobile device 18, which is generally a smart phone. While a smart phone is described here, it will be understood that any of the various electronic devices described above may be employed to receive and display sensor or other data and output results, as well as alerts and alarms based thereon. Moreover, the smart phone (or device with similar smart phone capabilities) may transmit displayed notifications, results, recommendation, alerts, and alarms, to various devices coupled thereto, e.g., via Bluetooth™. Such devices include head mounted displays like Google Glass™, watches, and the like.

The mobile device 18 runs a CGM application 209 by which various monitoring and display functions are provided, based on the signal received from the sensor electronics 12. As part of this CGM application, a decision support module 211, which may also be a processor module, is provided to perform the decision support functions described here. While a decision support module is described, it will be understood that such may be replaced by appropriate functionality to perform the methods described here. In some cases the functionality of the decision support recommendation module 211 may implemented as an application running as a subroutine within the CGM application or running as a parallel process within the CGM application.

The mobile device 18 includes a display 202 for displaying notifications, results, recommendations and alerts/alarms. While the display 202 is portrayed as a display screen, and thus generally renders results visually, it will be understood that notifications, outputs, results, and in more urgent cases alerts/alarms may also be communicated using other means, such as audibly. The same may be communicated as an audible version of displayed text or numerals. Alternatively, tones or other sounds, even songs or ring tones, may be rendered to the user as a discrete indication of their blood glucose level.

The mobile device 18 may further include memory 210 or storage 212 for retrieval and usage of historical data, including user-entered data, as will be described in greater detail below. As the mobile device 18 may be in network communication with various servers, historical data may also be retrieved from a network server 222. Besides historical data, the server (or other network source) may further provide other external data that may enter into a determination that leads to the notification presented on the display 202.

The display 202 may itself provide an interface for the user to enter data, e.g., using a touchscreen interface, and the same may also be entered via buttons and switches 204 and 206 respectively. In some smart phones and in many other computing devices, a separate keyboard may be employed for the same purpose.

Signal processing may occur using the sensor electronics 12, using the mobile device 18, or using a combination of the two. Signal processing may also be performed in the cloud, e.g., on the server 222 or other network source. In many cases, however, initial processing of the raw sensor signal, such as calibration, smoothing or filtering, is performed by the sensor electronics 12, and an application on the mobile device 18 transforms the signal received from the sensor electronics 12 into a value that is then indicated on the display 202.

Inputs to Decision Support Module

Figure 5:
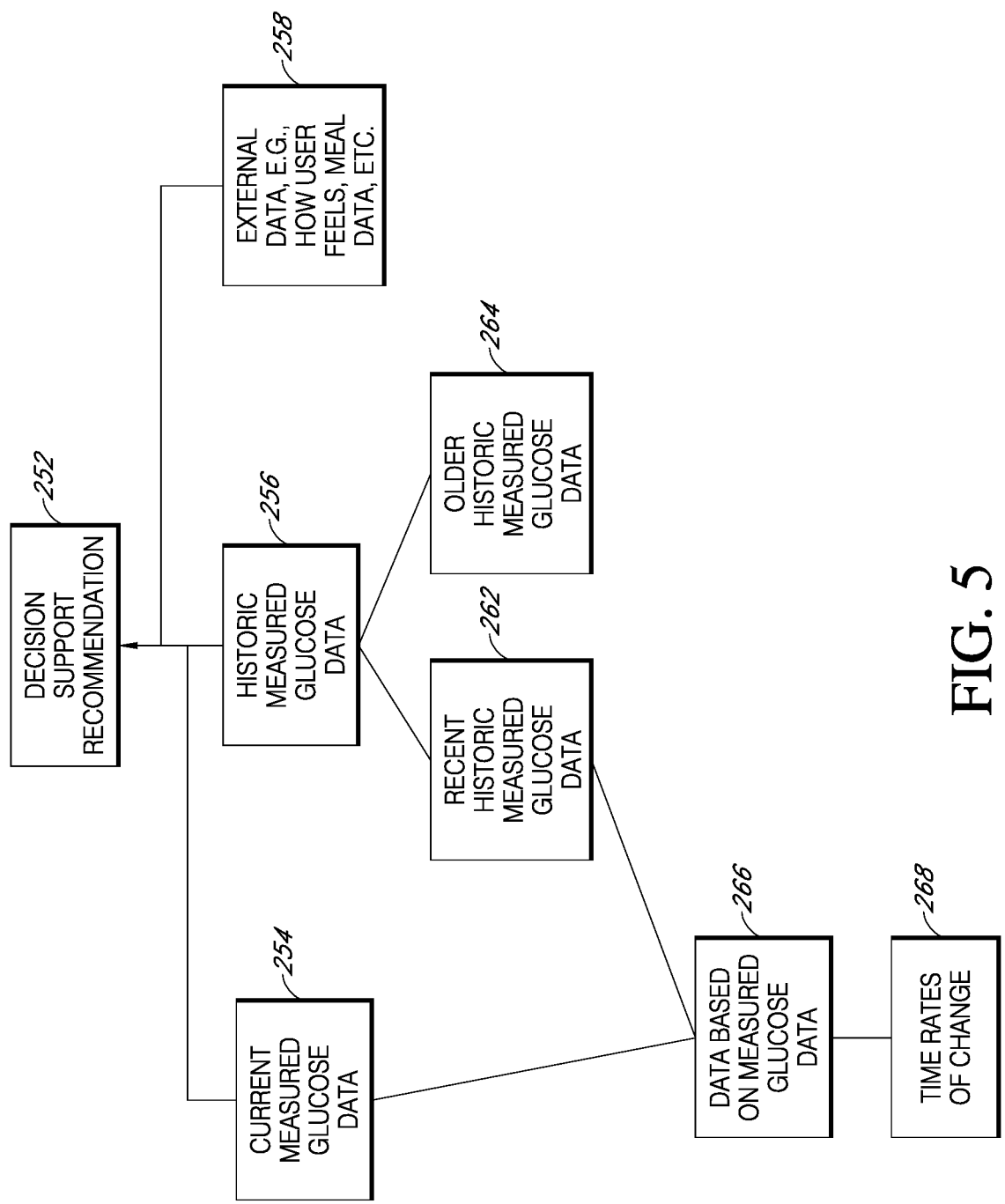
FIG. 5 depicts categories of parameters or variables which may be employed in the calculation of the decision support recommendation (DSR)

FIG. 5 illustrates how the measured blood glucose level can be combined with other parameters or variables to result in a calculated or otherwise determined decision support recommendation value 252, which is then presented on the display screen of the mobile device. The calculation or determination is generally performed by the decision support module 211 on the mobile device 18, but may also be determined in whole or in part by the server 222, or even in some cases by the sensor electronics 12. It will be understood that not all parameters and variables will enter into all implementations of determinations of the decision support recommendation value 252.

Various parameters and variables will be described, followed by examples of how the same may be combined to result in a decision support recommendation. Without intending to limit the scope of the arrangements in any way, it is believed that particularly useful combinations will include the current glucose value or combinations of glucose value and a first derivative of glucose value with respect to time. Numerous combinations are useful, however, as will be understood by one of ordinary skill in the art given this teaching, and thus the scope of the invention is not to be limited by the specific examples. In FIG. 5, the decision support recommendation 252 is illustrated as being based on at least data 254 corresponding to a current measured value of glucose, and/or data 256 corresponding to historic measured values of glucose, and/or data 258 which is not directly related to the measured values of glucose, and is thus termed "external data". The data 254 is generally the current measured value of glucose, e.g., as measured in mg/dL. The data 256 corresponds to historic measured values of glucose, and the same may be divided into data 262 termed "recent historic" measured glucose data and data 264 termed "older historic" measured glucose data. The recent historic data 262 may be that measured over the course of minutes or hours prior to the current measured glucose data 254, and thus may be particularly useful for current trending analyses. The older historic data 264 may be that measured over the course of days, weeks, months, or even years prior to the current measurement, and thus may be particularly useful in the calculation or determination of overall patterns or trends (data 262 may also be employed in this determination).

The current measured glucose data 254 and the recent historic measured glucose data 262 may be employed to calculate other types of data 266 based on current trends. For example, the same may be used in the calculation of data 268 corresponding to time rates of change of the glucose data, e.g., a first derivative with respect to time, a second derivative with respect to time, and so on.

The data 258 may correspond, e.g., to past or present user indications of how the user feels, what the user ate, and so on. Thus, the data 258 may bear an indirect correlation with glucose levels, but the same are not directly based, in the functional sense, on the measured glucose values. The data 258 may also constitute numerous other variables, as will be described below.

Various parameters and variables are described below that are based on the above types of data. Again it is noted that the determination of a decision support recommendation in a particular implementation need not include all the various types of data described, and in many cases will only include two or three types of data. Moreover, as the below description is only exemplary, data types other than those described below may also be employed. In particular, the calculation of a decision support recommendation may be performed by an algorithm, e.g., on the mobile device, as described above, and the algorithm may take into account several or numerous variables in its determination of the decision support recommendation. While these variables will be evaluated algorithmically at or near the same time, the below description in part discusses the effect of the variables sequentially, on each other, and on the determined decision support recommendation. In connection with a user interface for an electronic device such as a smart phone, the calculated decision support recommendation leads to a notification presented on a user interface of a mobile device, and which in some cases may further lead to an "actionable alert" (or alarm) which is displayed to the user and which suggests one or more actions to be performed. In some implementations, the notification seen by a user may simply be an indication of the user's status, e.g., that the user is in a normal state and no action need be taken. In other cases, the presentation may be of an alert or alarm condition. By unlocking the mobile device, performing a "swipe" action, or otherwise "drilling down" to the data underlying the existence of the alert or alarm condition, the user can view the unambiguous actions to be performed.

A first type of data that may be employed, and one that is involved in most implementations, is a measured value of glucose. This first type of data may be in numerical form, with units of mg/dL or otherwise, or may be processed or transformed to derive another type of data, generally correlated with the glucose value. In some cases, the first type of data may also be employed in its raw form, as received from the sensor electronics without significant processing and/or processed by the sensor electronics. Processing if desired may then be performed on the mobile device (or other device) running the decision support module or related application to determine the decision support recommendation. The first type of data may further be received from an intermediate module or transformation, e.g., may be received from another application running on the smart phone. Generally this first type of data may undergo processing, e.g., to calibrate, smooth, filter, or otherwise "clean up" the signal representing the data.

While generally a current measured value of glucose is employed, it will be understood that the first type of data may also include one or more past values of glucose, or even future values of glucose as determined by a prediction algorithm. Additional details of prediction algorithms are discussed below.

In the decision support recommendation determination, all other factors being equal, a high glucose level tends to indicate a hyperglycemic state. In this case a decision support recommendation may present to the user any of a variety of recommendations such as suggesting the patient hydrate, exercise or take a suitable medication. Conversely, a low glucose level indicates a hypoglycemic state. In this case a decision support recommendation may suggest, for example, that the patient eat a snack. Of course, numerous other schemes will also be understood and may be employed given this teaching.

Other types of data may be based on this first type of data, e.g., the first derivative of the glucose values with respect to time can be employed to determine a time rate of change of glucose value, i.e., a "velocity" of the glucose value, i.e., if the glucose value is increasing or decreasing, as well as how fast such changes are occurring. Thus, a data value representing the first derivative can be employed in an initial estimate of a prediction of future glucose values, and also in the determination of the decision support recommendation. Additionally, the direction and amplitude of the first derivative may be used to determine a weight of the same information in the determination of the decision support recommendation.

Figure 6B:
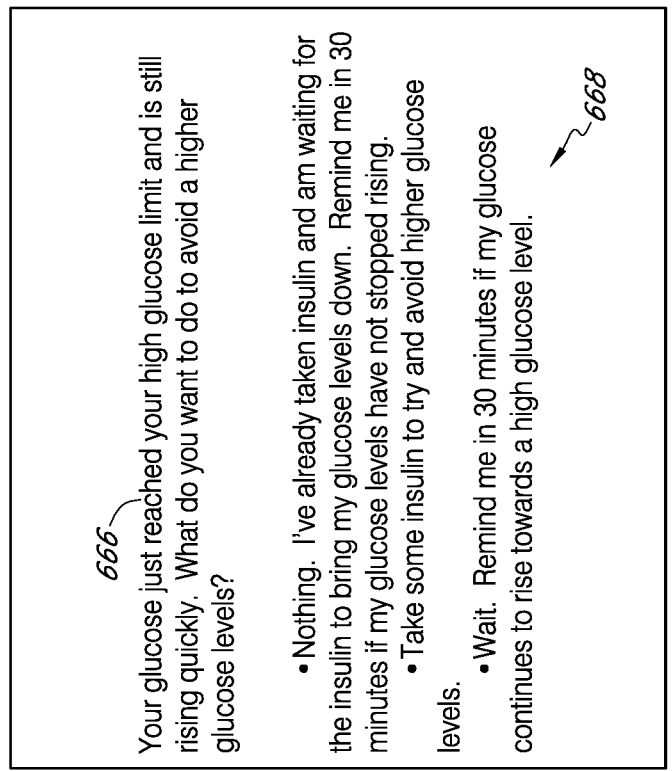
FIGS. 6A-6B are exemplary user interfaces on which a decision support recommendation prompt is presented.
Figure 6A:
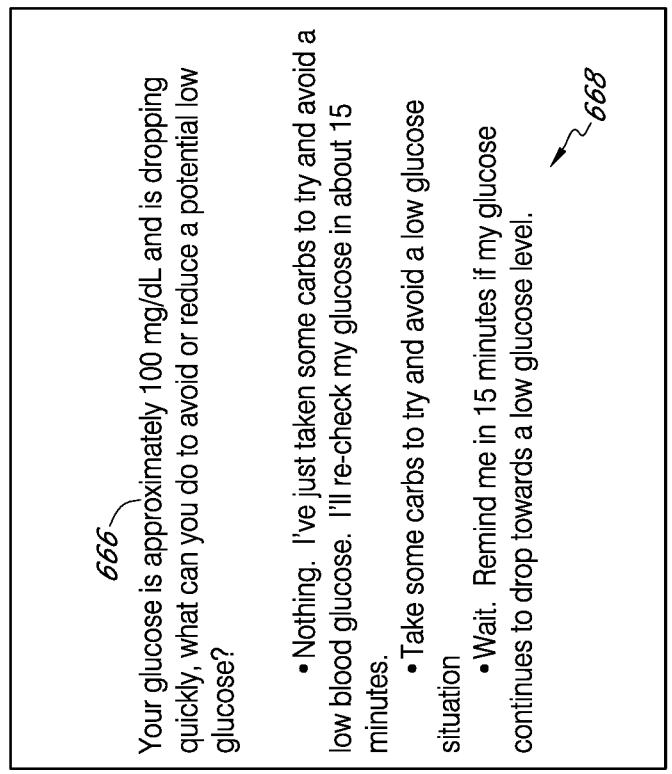

FIGS. 6A and 6B illustrate examples of decision support recommendations that may be presented on a user interface 730 of a mobile device, which employ as input data the glucose level and its first derivative. In these examples, a current situation 666 of the user's state is presented. In addition, for each situation one or more recommendations 668 is presented. In the examples of FIGS. 6A and 6B, three recommendations 668 are presented for each situation 666. In some embodiments the recommendations may be ordered based on most safe to most aggressive.

The first derivative of the glucose value, as well as higher order derivatives, particularly with respect to time, requires a certain amount of historical data to be stored and used in a calculation. Such data is generally based on recent historical data, but it will be understood that older historical data may also be used and may also provide useful information with regard to user patterns, as will be described below, where such user patterns may be analyzed in the abstract or with respect to, e.g., time of day.

Another type of data that may be based on the glucose value, and for that matter on the first derivative, is the second derivative of the glucose value with respect to time, i.e., the acceleration. Such provides information about the speed with which changes in glucose level are occurring, and can often advantageously be employed to determine to what extent changes in glucose level will stabilize or will lead to excursions from desirable values.

In some implementations, the determination of a decision support recommendation may be based, at least in part, on the measured glucose value and the first or second derivative with respect to time of the measured glucose value, or both. In some implementations, the calculation of the decision support recommendation may be based on the factors above in combination with other factors, described below. For example, the glucose value, in combination with another type of data based on the glucose value, e.g., a time derivative, may be employed in combination with duration data (discussed below) to determine that a state has been reached for which a DSR should be provided to a user. In the same way, the glucose value and/or a time derivative may be employed in combination with food ingestion data to determine if a decision support recommendation should be made.

Returning to types of data based on glucose values, such may further include higher order derivatives with respect to time, glucose trace graphs over a period of time, the level and duration of the last significant glucose value excursion, e.g., a level of the last glucose peak, and so on.

The duration over which a measured glucose level occupies a predetermined range is yet another type of data which may be employed in calculations, and the same may be determined by analysis of the glucose values and in particular values over time. The predetermined range may be arbitrarily-defined, but generally may indicate a particular state, e.g., high or low hyperglycemic, high or low hypoglycemic, or euglycemic.

In more detail, the time in which a user spends in a range corresponding to a particular state may provide an important input to the decision support module, as the same may indicate that a therapeutic intervention is necessary, especially where the states are those of hypoglycemia or hyperglycemia. For example, if the user has a low glucose level, but the duration of a relatively low hypoglycemic event is considerable, then a decision support recommendation to eat a snack may be presented based on the duration, as excursions further downward become that much more likely. In using duration as a factor, the decision support module may use as an input the duration itself, or a time over which a particular state has exceeded a threshold duration, or other related parameters. Such data is generally available via an analysis of the stored glucose values over time.

Another type of data which may be employed in calculations or determinations of decision support recommendations corresponds to recent or historic events, and in particular large excursions from an expected or a baseline value of glucose level. In particular, users who have had recent significant excursions are generally more likely to have significant current or future excursions. To address this problem, the decision support module may take account of such prior historical events in the determination of the decision support recommendation. For example, the level of the last glucose peak, or its duration (as measured as a time period over a threshold level or within a range), or the like, may be employed in such determinations. The level and/or duration of the last significant excursion or deviation of glucose values away from a baseline (or an otherwise expected value) may be employed in the determination as the same are often indicative of a user's current risk of a glycemic excursion, and in particular are an indicator of a greater likelihood of future excursions or deviations. As a subset of this data type, the "last hypo/hyperglycemic event", including its level and duration, may be employed in the determination. In any event, such data is generally available via an analysis of the stored glucose values.

A further type of data which may be employed in decision support recommendation determinations employs older historic measured glucose values. In one case, and as mentioned above, patterns of glucose values may be determined and employed to inform a baseline from which, e.g., excursions are measured, which may constitute significant deviations from the baseline. The pattern data may be partially time or time-of-day-based, but are not necessarily so. In particular, users often follow very regular patterns based on eating, sleeping, exercising, or other activities which can bear on glucose levels, such activities occurring at certain times of the day. These can be advantageously employed in determining whether excursions are expected outside normal levels. If the time of day confirms a pattern, the determined decision support recommendation can be more predictive, confident, and can provide more useful feedback. Such pattern data is generally available via an analysis of the stored glucose values.

For example, a user may generally experience a lower glucose value in the morning than in the afternoon. The decision support module may adapt to this pattern, and expect a lower reading in the morning and a higher reading in the afternoon. Similarly, the user may typically consume a meal of oatmeal in the morning, and thus cause a spike in their glucose value. The decision support module may determine that such a meal at approximately the same time every morning constitutes a pattern, and may simply be considered and thus not require a decision support recommendation. Considering the patterned values of the baseline would thus cause analysis of the spike to not be labeled a spike at all. Of course, other factors bear on the calculation of a decision support recommendation, and they as a combination may determine that a decision support recommendation should be made.

If the user's sleep pattern is known or can be determined by the decision support module, a recommendation can be presented to the user, for instance, suggesting a type of food that may be eaten before sleep or between dinner and sleep. While eating and sleeping have been disclosed elsewhere herein, it will be understood that patterns may be recognized or generated and employed in the decision support recommendation determination for other events, such as meetings, work, exercising, and the like. Time-of-day information may be captured from any clock circuit or application, such as those from a server, or from the mobile device or sensor electronics. Patterns may be based on detected events occurring with any sort of periodicity, such as during a cycle of a day, week, or month. Such data is generally available via an analysis of the stored glucose values, and various pattern recognition software applications may be advantageously employed. In some cases, a pattern may be detected, and a user may be prompted to determine if there is a particular cause for the pattern, e.g., a common mealtime, an exercise class occurring at a usual time, and the like. Such prompts may be particularly used when the decision support module is using machine learning to determine daily or other periodic patterns or behaviors of a given user.

In this same way, deviations outside a recognized pattern may cause a similar user prompting. For example, a deviation may cause the decision support module to ask the user "what did you do differently?". Such may allow analysis and disambiguation of, e.g., a missed bolus versus an insufficient bolus.

Such pattern data may even provide prospective recommendations. For instance, pattern data may be employed to suggest to a user where their glucose level is heading, based on past historical data and as a consequence a decision support recommendation may be made. For example, the decision support module may send a warning such as "it's almost 2 PM and we know at 2 PM you are often low. You should review X and take possible action Y", where X is a user-understandable variable such as glucose level and Y is an appropriate action to take given the current determined decision support recommendation.

It will also be understood that other types of data may be employed related to deviations from normal glucose patterns but which are not necessarily time-based. Such may include where exercise (detected by motion or heart rate, for example) is usually associated with a lowering of glucose level. "Normal glucose patterns" may be learned for a specific user using known pattern recognition algorithms. A deviation from such normal patterns may then be defined and employed as an input into the determination of the decision support recommendation. In some cases, a glycemic event outside the norm may be a predictor of a higher risk state, at least in part, due to the unexpected nature of the event, which might dictate a different type of output to the user, i.e., a different type of recommendation rendered on a display of a mobile device, or output to an insulin delivery device, i.e., pump. In this way, the problem of treating non-time-based patterns may be effectively addressed.

Other types of data based on glucose values, or glucose values as measured over time, will also be understood. For example, a glucose trace over a recent time period, e.g., six hours, may be employed to inform current decision support recommendation calculations or determinations.

Other types of data may be employed in the determination of the decision support recommendation, and which are not based on glucose values. A first category of types of such data are those based on data from other sensors or sources, or entered by the user. For example, the data may be of a type including anthropometric data, e.g., corresponding to body measurements such as BMI or weight. Anthropometric data may be particularly important for Type II diabetes patients, but may also have some bearing for Type I. In particular, for Type II diabetes patients, changes in anthropometrics may have a significant bearing on the decision support recommendation determination. For example, an improvement in BMI for a Type II patient should translate into a better decision support recommendation on average, all other aspects being equal. Anthropometric data measurements may be captured semi-automatically, e.g., via a connected weight and height scale, or the values for such BMI calculations can be entered manually by the user, e.g., in the user interface of the mobile device. Measurements may also be imported from other systems, including from the cloud. In this way, the problem of treating all users the same, no matter their anthropometric data, may be effectively addressed and resolved.

Another type of data which may be employed in the determination of the decision support recommendation is user activity level, in particular data about the amount of activity, the type of activity, and a duration of the activity (or a combination of these). In particular, quantification of user activity levels generally may provide a better understanding of glucose value trends. Activity information can feed into the determination of the decision support recommendation, and may also be useful to present to a user desiring to receive additional information as to why a particular decision support recommendation is being made. Such may also be employed to determine what sorts of questions may be asked to assist the user in managing their diabetes.

Measurement of the activity level may be via accelerometer, GPS data, or even WiFi data indicating location. Many mobile devices are able to, e.g., count steps, and more generally to determine whether the mobile device user is stationary, walking, running, driving, or the like. It will be understood that such data may be entered manually as well, e.g., miles run, walked, or biked.

A related type of data is information about exercise, which in general is beneficial for diabetes patients, and can help prevent hyperglycemia and hypoglycemia as well as assist in the management of insulin delivery. However, exercise sometimes has long-term effects on diabetes, and can cause severe hypoglycemia hours later in certain users. Accordingly, it is occasionally difficult to identify exercise as a cause of hypoglycemia because of this long time lag. If exercise can be accurately detected, such as by using the measurement devices noted above, predictive analytics may be employed to predict when it may begin to affect the glucose value and thus the associated risk state which may require a therapeutic intervention that can be recommended by the decision support module. For instance, the decision support module may recommend that the user eat a snack before or shortly after an exercise session, particularly if the level of exertion during the session is particularly high. Alternatively, or in addition, a recommendation may be presented to reduce the intake of insulin over the next several hours since exercise can change insulin sensitivity. Exercise can be monitored using generally the same types of devices employed to monitor activity, and may include parameters such as the duration of exercise, the type of exercise, the amount of calories burned, and the like. It will be understood that such data may be entered manually as well.

A further related type of data corresponds to sleep information. In particular, diabetes users are known to be more likely to undergo an undetected hypoglycemic event while sleeping. Motion, or the lack thereof, as well as other factors, may be employed to detect sleep and correspondingly evaluate risk. Other factors may include, e.g., heart rate, user input, and the like. The monitoring device, e.g., a mobile device running a decision support module, may be equipped with a "night mode" feature or module, instantiatable by the user, which may be employed to assist in the detection of sleep. Motion detection for such purposes may be performed as noted above, e.g., by use of an accelerometer worn on the body. For example, a CGM sensor or transmitter may incorporate such an accelerometer or other motion detection circuit. A phone or other motion detector placed adjacent the user can detect how often the user moves, again indicating sleep. In some cases, an alarm system's motion detector may be employed to provide such information and data. A heart rate monitor can measure changes in the user's heart rate. The user interface of the mobile device may be employed to assist in the detection of a sleep state as well. For example, if a user is not interacting with the mobile device at all, as determined by button presses, swipes, or other like interactions, such may be associated or consistent with a state of sleep, or the same may be learned by the decision support module to be associated with such a state. Conversely, if a user is interacting with their mobile device, it may be assumed the user is not sleeping. If the mobile device running the decision support module is equipped with a "sleep mode" function, the user may activate such, in which case no assumptions about sleep or sleep detection is necessary.

Such a "sleep mode", "night mode" or sleep detection functionality may afford a number of advantages in certain implementations. In particular, by assigning a higher risk state to a glycemic event during the night versus during the day, the system understands that the user is more likely to be unaware of their diabetic risk state, and thus the glycemic event should be handled differently. In this way, the problem of user inattention during sleep, or excursionary values of glucose encountered during sleep, may be effectively addressed.

Another category of types of data employable in the decision support recommendation determination corresponds to physiological data. One such physiological data type includes hydration information. In particular, dehydration is often associated with high blood glucose levels. Accordingly, the same may be employed to further inform the decision support recommendation determination. Hydration information may be received from, e.g., a Tanita BC-1000 body composition monitor in combination with a Garmin™ Connect system. It will be understood that such data may be entered manually as well, at least at a qualitative level.

Another such physiological data type includes heart rate information. Heart rate can be indicative of exercise or indicative of other factors such as stress. Where heart rate or changes therein are due to exercise or other activity, the activity monitors noted above may be employed to quantify the same. Alternatively, heart rate may be communicated wirelessly from a heart rate monitor or other application. In another implementation, the same may be entered manually by the user, using indications such as "high heart rate", "normal heart rate", and the like, or quantitative values if the user can measure such.

Another such physiological data type includes blood pressure information. In particular, the effect of diabetes on blood vessels tends to heighten the risk of high blood pressure. Accordingly, monitoring the same can be useful and can be factored into the determination of the decision support recommendation. Various body-worn blood pressure monitors are available, and the same can, in a wired or wireless fashion, communicate blood pressure data to the device running the decision support module. Alternatively, users may measure their own blood pressure and enter the same manually into the device.

A further physiological data type includes body temperature. Body temperature is often an indicator of illness, which can in turn affect the diabetic risk state and thus the decision support recommendation. For example, the body temperature and/or underlying illness may cause the glycemic response to various inputs or therapies to be different from what is expected in other users, or from what is expected historically from the same user.

The body temperature data type can be captured by introducing a temperature sensor into the sensor patch or by the use of other such thermometers. This and other types of body temperature monitors may be found in U.S. patent application Ser. No. 13/747,746, filed Jan. 23, 2013, and published as US 2014/0005508A1, entitled "DEVICES, SYSTEMS, AND METHODS TO COMPENSATE FOR EFFECTS OF TEMPERATURE ON IMPLANTABLE SENSOR", owned by the assignee of the present application and herein incorporated by reference in its entirety. Temperature information may also be input manually qualitatively or quantitatively.

Another type of data that may be employed in a decision support recommendation determination is context and behavioral information. In particular, such information may correspond to how a patient uses their mobile device, and thus gives context to certain data determined by the device. Behavior input information may be obtained via the system and can include an amount of interaction, glucose alerts/alarms states, sensor data, number of screen hits, alarm analysis, events (e.g., characteristics associated with the user's response, time to response, glycemic control associated with the response, user feedback associated with the alarm, not acknowledging alerts/alarms within X minutes, time to acknowledgment of alerts/alarms, time of alert state, and so on), diabetes management data (e.g., CGM data, insulin pump data insulin sensitivity, patterns, activity data, caloric data), data about fatty acids, heart rate during exercise, IgG-anti gliadin, stress levels (sweat/perspiration) from skin patch sensor, free amino acids, troponin, ketones, adipanectin, perspiration, body temperature, and the like. The inputs may be provided by a sensor in data communication with the monitoring device. In some implementations, the information may be obtained through an intermediary such as a remote data storage.

Contextual information which may be provided as an input for determining a decision support recommendation includes a person's biology, location, sensing surroundings (e.g., light, sound level), environmental data (e.g., weather, temperature, humidity, barometric pressure). The inputs may be received via a peer-to-peer or a mesh network via machine-to-machine communication. Context information can include daily routine information (which may change especially from weekdays to weekends) obtained from a calendaring application. Context information can include a frequency of touching or grabbing the monitoring device, even if not interacted with, based on a sensed motion of the device.

Photos can provide contextual information. For example, photos of one or more of: a glucose meter reading, an insulin pen or pump JOB, a location (e.g., a gym, park, house, Italian restaurant), or a meal may be used to provide context information. The photos may be processed to identify, for example, caloric intake for the meal shown in the photo. The type of insulin used may also be provided to the monitoring system as a useful input to the decision support recommendation determination. Context may also be provided by basal or bolus settings provided to or determined by the monitoring device.

Other inputs to the decision support recommendation determination which constitute context/behavioral data may include data types referenced elsewhere in non-context/behavioral inputs, such as exercise information from a fitness bike or the like, glucose sensor information from a blood glucose (BG) meter or CGM, insulin delivery amounts from insulin delivery devices, insulin on board calculations for the device, and other device provided or calculated information. Other context/behavioral data inputs to the decision support recommendation determination may include: hydration level, heart rate, target heart rate, internal temperature, outside temperature, outside humidity, analytes in the body, hydration inputs, power output (cycling), perspiration rate, cadence, and adrenaline level, stress, sickness/illness, metabolic/caloric burn rate, fat breakdown rate, current weight, BMI, desired weight, target calories per day (consumed), target calories per day (expanded), location, favorite foods, and level of exertion.

For any of the above referenced behavior or contextual inputs, the system may be configured to receive and/or generate analytical metrics based on the inputs. For example, a composite value may be generated based on the glucose level, temperature, and time of data generated index value for the user. The composite value may then be considered in the determination of the decision support recommendation.

This information can be collected from various sensors within or outside of the device, such as an accelerometer, GPS, camera data, and the like, as well as third-party tracking applications, including sleep cycle applications. For example, such tracking applications may employ geolocation to determine context and behavior. Moreover, context and behavior may also be determined by use of social networking information available about the user, where a social networking feed, associated with the user, is arranged to provide a source of data to the decision support module and/or for providing output thereto.

Other types of data which may be employed in the decision support recommendation determination include information about food and drink ingested, and insulin. Variables or parameters pertaining to these data types may include information about their amounts, their types, and the time and duration over which they were received.

In the case of food and drink ingested in meals, such may be captured in a number of ways, e.g., manually by a user entering food and drink information into the device, e.g., on a spreadsheet, using the camera on the mobile device to capture a photograph of the meal, or by entering data from third-party food applications, which may allow, e.g., food items of a given restaurant (having data already entered in the application) to be "checked off" and entered into the determination as they are consumed. In some cases, users may be prompted for such information, e.g., if the device detects a spike in glucose level. Meal data may even be hypothesized (subject to confirmation by the user) by use of GPS or social networking data indicating that a user is near, or has "checked in" at a known favorite restaurant. The user may be prompted to confirm that they have ordered their "usual meal", which may then automatically populate food data with the parameters of that meal or alternatively the prompt may provide an opportunity to enter other food choices if the user has deviated from their usual option. Generally meal data may be provided with details such as the amount ingested, the time of ingestion, and other meal data which allow a clinically significant determination of the decision support recommendation. Using such information, problems currently encountered in diabetes care based on the lack of such (and other factors) may be effectively addressed.

In some cases inputs to the decision support recommendation determination such as food and drink ingested may be obtained by automatically aggregating data from third party applications without the need for the input data being manually entered by the user. For instance, if a user uses a third-party application or a web browser on his or her display device to e.g., check into a restaurant, order food for pickup or delivery, or click a photo of a food post on Instagram, this information may be provided to the CGM application on the display device. This input data may be used by the decision support recommendation algorithms to provide relevant, contextual information and insights to the users. For example, when the user checks into a restaurant that has been previously visited and this data is automatically provided to the CGM application, this data may be correlated with other available data to advise the user e.g., that the last time they ate at this restaurant they average glucose level was 189 mg/dl. In this way information may be obtained from the user's existing application usage without placing any additional burden on the user by requiring him or her to enter the same information into the CGM application. Such inter-application communication can also occur between the CGM application and the third party applications that are associated with other devices such as a smartwatch or fitness tracker.

Another variable or parameter which may factor into the decision support recommendation determination is a level of insulin. The data may be provided directly from an integrated insulin pump or from EMR in the cloud. Such data may include information about the amount of insulin on board, insulin sensitivity, and past, present, and future planned basal and bolus levels. Data may be obtained by sensor data or other electronically communicated data, or may be provided by user entry. One type of information which may be obtained from this data includes the time between an insulin bolus and a meal peak, which can be determined using insulin information and glucose information.

A further type of data which may be employed in the decision support recommendation determination corresponds to stress level. In particular, stress is known to affect diabetes and thus to affect a user's risk state. In some cases, such data may be provided via a sensor, but in other cases is captured by asking the user to choose from various emoticons or other indications of emotion. Such may also be inferred from other sources, by analysis of events on a user's calendar or other regularly scheduled activities, e.g., work, exercise, family time, or the like. Stress data may include information about the amount of stress, the type of stress, and how long the stress lasted.

A related type of data which may be employed in the decision support recommendation determination corresponds to current health, which may have overlap with current emotional state. Such measurements can be captured manually, via the device, including by using the same sort of emoticons noted above with respect to stress, or may be imported from information in the cloud. Current health and emotion are known to have a significant impact, particularly on Type II glucose control and insulin resistance, similar to anthropometric data. Health data may include information about a current illness, the severity of the illness, how long the user has suffered with the illness, and so on.

Demographic data may also be employed such as age or gender. In particular, demographic data may be collected from online stores, network or cloud sources, or manually entered into the device, and such may provide useful information in the determination of the decision support recommendation. For example, it is known that pediatric users are more prone to faster and higher glycemic swings. As another example, it is believed that the risk state of a user, particularly in older users, and particularly those with Type II diabetes, may have higher risk states with certain glycemic excursions as compared to younger users with the same glycemic excursion.

Another factor which may be employed in the decision support recommendation determination is the sensor site location. In particular, in some cases the site or location of a CGM sensor may lead to maintained distinctions in blood glucose level with respect to such locations. These distinctions may be factored into determination of the decision support recommendation. Such data is generally entered by the user manually, although historic data may be employed to avoid such user input, if such is regular and thus if an unambiguous determination may be made. Additional details about the use of sensor site location may be found in U.S. Patent Application Ser. No. 61/904,396, filed Nov. 14, 2013, entitled "INDICATOR AND ANALYTICS FOR SENSOR INSERTION IN A CONTINUOUS ANALYTE MONITORING SYSTEM AND RELATED METHODS" and U.S. Pat. No. 9,480,401 claiming priority to same, owned by the assignee of the present application and herein incorporated by reference in their entirety.

Another factor which may be brought to bear on the decision support recommendation determination is the cause, if known, of a rise or decrease in blood glucose level. In this regard it is noted that some changes in glucose level are brought on by stress and others by food intake. Such data may be preprocessed or pre-associated prior to its input into the decision support module, or may be associated therein. For example, food data may be processed in combination with glucose levels to determine whether a glucose rise resulted from food or from another cause, such as stress. Using such data, problems seen in the past with a lack of consideration of such causes and effects may be effectively addressed.

Glucose values (and derivative data) may be weighted by the decision support module based on signal quality, confidence level, and the like. Such would generally be performed automatically, by the electronic device, based on analysis of the signal data from the sensor electronics. However, any of the above variables or parameters could enter the decision support recommendation calculation in a weighted fashion, where the weighting is performed automatically, e.g., by signal analysis from the underlying sensor, e.g., accelerometer, weight scale, etc., or by using data entered manually from, e.g., a physician or the patient.

A summary of the described types of data is provided in Table I below. Note that certain parameters and variables occur in more than one data category.

user interface of mobile device that runs a CGM application. Alternatively, or in combination, various types of advanced outputs (additional processing or additional detail regarding the decision support recommendation processing (e.g., information about inputs) may also be provided (step 282).

TABLE 1

| DATA CATEGORY | SUBCATEGORY | PARAMETER OR VARIABLE |
|---|---|---|
| Current Measured Historic Measured Glucose Values, e.g., data of a second type | Glucose Value Recent Historic Measured Glucose Values, and data derived from recent historic measured values | Current measured glucose value, e.g., data of a first type First derivative of recent glucose values, e.g., velocity (sign and amplitude/rate of change of glucose concentration) Second derivative of recent glucose values, e.g., acceleration of glucose concentration Higher order derivatives of recent glucose values Glucose trace over last x hours, e.g., 6 hours Level of last glucose peak, level/duration of last significant glucose value excursion, e.g., recent local maxima or minima in glucose levels Predicted values or ranges of glucose data Weighting of inputs based on calculated accuracy, confidence level, or noise information, e.g., based on quality of glucose data Other data, including processed glucose sensor data, e.g., duration of levels of values (stable or increasing/decreasing) Recent (or last) events, e.g., significant events (e.g., within the last 24 hours), which may indicate likelihood of future events. Amount of filtering, smoothing, and other data processing, especially with respect to lag Duration of current urgency state |
| External Data, e.g., data of a third type | Older Historic Measured Glucose Values Data from other Sensors/sources Data input by user | Patient pattern data Deviation from normal glucose patterns (similar to time of day, but not necessarily time-based) Anthropometric data Activity level, e.g., determined or calculated by GPS or an accelerometer within the mobile device, e.g., sleep or exercise Physiological data, e.g., heart rate, temperature, blood pressure, hydration Food data received from an app running on a mobile device -patient enters data in the app or app predicts data based on historical data, e.g., what the patient has at a given restaurant before, the identity of the restaurant determined by a user check in, GPS, and so on. Food data may also be entered via the mobile device camera. Insulin information, such as from a pump or EMR in cloud Context/behavior data Time of day and patient pattern data Level of user interaction Age, gender Weighting of any of the inputs - a user may also weight the measured inputs Patient indication of activity level, e.g., exercise Patient indication of food/drink ingested Anthropometric data Insulin information Stress level Current health Age, gender Sensor site location |

Figure 7:
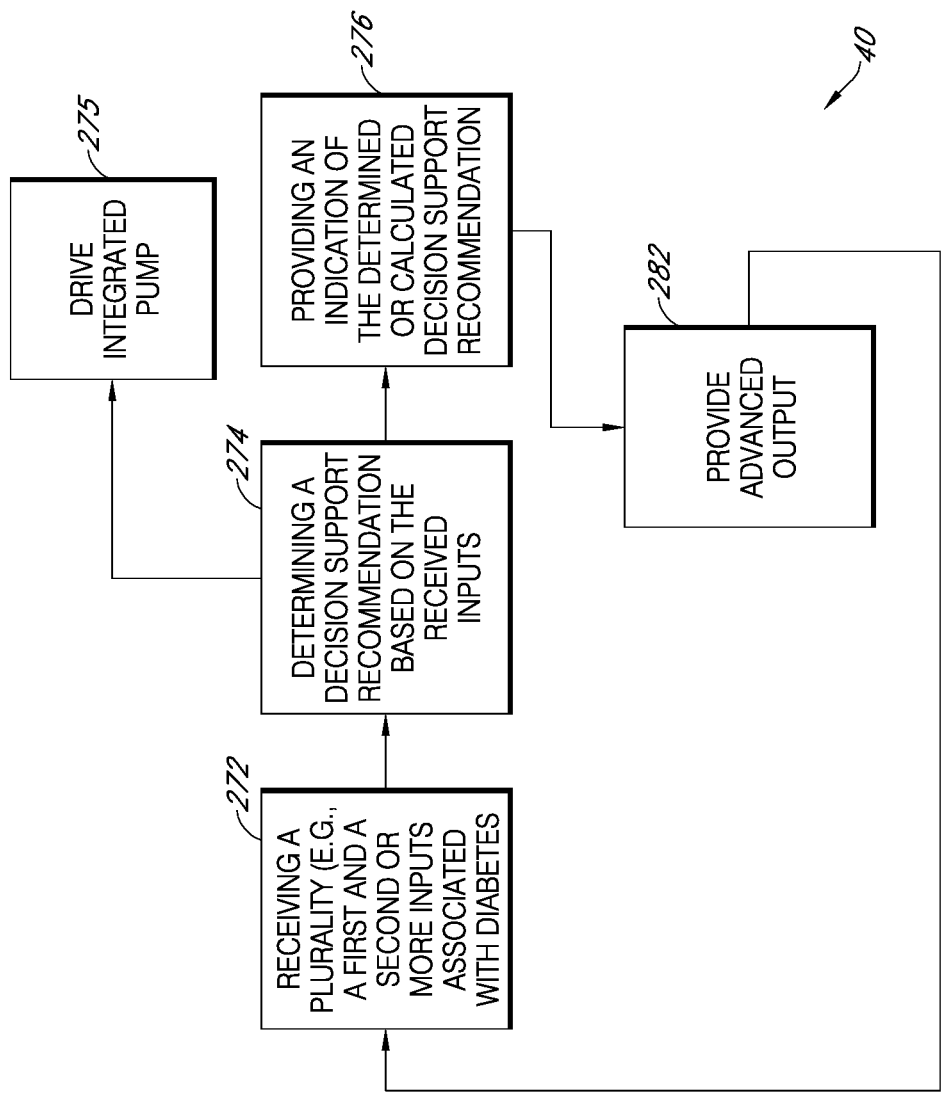
FIG. 7 is a flowchart illustrating a method according to present principles.

FIG. 7 shows a flowchart 40 illustrating general use of the parameters and variables discussed above. In a first step, a plurality of inputs are received associated with a malady such as diabetes, the inputs corresponding to variables or parameters, which may be measured, may be entered by a user, or otherwise obtained, e.g., via the cloud or other source (step 272). A decision support recommendation is then calculated based on the received inputs (step 274). The decision support recommendation may be determined or calculated in a number of ways as will be described below. A next step is to provide an indication of the decision support recommendation (step 276), such as an output. The output may be presented, for example, on a display or other In some implementations, the determined decision support recommendation may serve to drive an integrated pump for a medicament (step 275).

Figure 8:
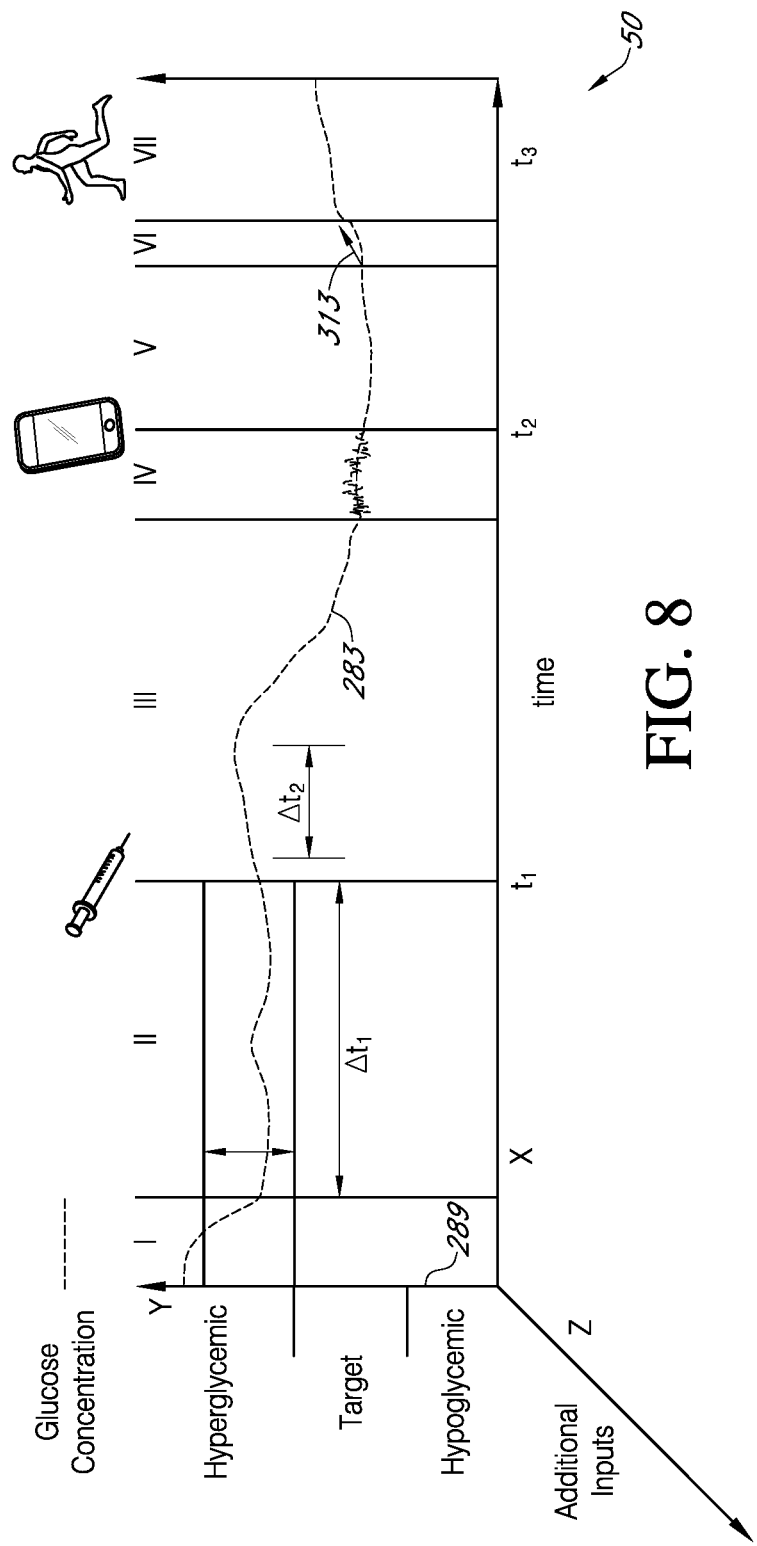
FIG. 8 is graph of various input data items as a function of time, which may be used to determine a decision support recommendation.

FIG. 8 shows a graph of various input data items as a function of time, which that may be used to determine a decision support recommendation. For simplicity of illustration only a single input parameter is presented, which in this case is the measured glucose level, which is represented by trace 283 along the x and y axes, where the x-axis shows the time and the y-axis shows the glucose level. As shown, additional inputs are indicated as being along the z-axis to illustrate that in more complex examples the trace 283 may be a multidimensional trace that takes into account a series of different inputs that may be used by the decision support module to determine a decision support recommendation. Examples of such inputs have been discussed above.

As may be seen in FIG. 8, in Region I a user is initially in a hyperglycemic state, and has a GUI in the low to medium range. In Region II, the glucose value is seen to be occupying a range of hyperglycemic values (e.g., 180-400 mg/dL) 293 over a period of time $\Delta t_1$. If the time $\Delta t_1$ exceeds a predetermined threshold, and the case of FIG. 8 assumes so, the decision support module may present at time $t_1$ a recommendation to the user to inject a bolus of insulin in order to mitigate the hyperglycemic event. After a delay of a period of time $\Delta t_2$, the glucose concentration begins to decrease in region III. Region IV indicates a region in which the glucose value has, for one reason or another, become noisy, and thus a low confidence level may be associated with that section of the signal. Accordingly, the decision support module provides a recommendation at time $t_2$ to the user suggesting potential actions that may be taken to reduce the noise, such as checking the placement of the sensor, the quality of the communication link between the sensor and the mobile device, and so on. Continuing further along in time, region VII indicates the user is heading towards a mildly hyperglycemic state and hence the decision support module, based on the trend in glucose levels as well as knowledge of the user's recent activity level and exercise patterns, makes a recommendation at a time $t_3$ suggesting that the user exercise.

Safety Module Based on Reliability of Inputs to Decision Support Module

As previously mentioned, it is vitally important that any decision support recommendations that are made, particularly if they involve therapeutic interventions, be as safe as possible with minimal risk of harm to the user. Even if the recommendations strictly conform to clinically established guidelines, there is still a risk that a particular recommendation may in fact be unsafe. One potential reason for this is because one or more of the inputs to the decision support module may be inaccurate or otherwise unreliable, thereby leading to an inappropriate recommendation because the user's actual or predicted state or condition is misinterpreted. The reasons why any particular input may be unreliable will vary depending on the nature and source of the input, as well as a variety of other factors. Illustrative examples of these factors for some of the types of inputs previously discussed will be presented below.

In accordance with present principles, a reliability level or rating may be assigned to each input that is used by the decision support module. The assignments may be pre-set in the factory or they may made by algorithms employed by the decision support module itself and/or by a cloud-based processor in communication with the decision support module. As used herein the term reliability in some cases may encompass any uncertainties in precision or accuracy that may be known to be associated with measurements from individual sensors and the like. Additionally, or alternatively, the term reliability in some cases may encompass any uncertainties in the relationship between any of the input data items that are used in determining a decision support recommendation and the diabetic state of the user.

The reliability level may be a numerical index, with say 1 representing a very unreliable input value and 5 representing a highly reliable input value. The reliability level may alternatively be categorized qualitatively by reliability buckets representing low, medium or high levels of reliability, for instance. Of course, other quantitative or qualitative reliability indices may be envisioned as will be appreciated by one skilled in the art. The reliability levels that are assigned may reflect absolute or relative levels of reliability. In some cases the reliability levels may be factory set. In other cases various analysis frameworks such as machine-learning, for example, may be used to either establish a reliability level for a given input or to modify a previously established reliability level that may have initially been factory set.

One factor that may be used to determine the reliability levels is the source of an input data item. For example, all else being equal, input data that is received directly from a sensor e.g., an analyte sensor, a temperature sensor, etc., may be assigned a higher reliability level than input data that is manually entered by the user. Likewise, an input data item that is received from other devices (external to the CGM system) or other applications may be treated as more reliable than a manually entered input data item. That is, manually entered data may be treated as being less reliable than data that obtained through machine-to-machine communication.

For example, an amount of physical activity expended during an exercise session that is obtained from motion sensors, accelerometers, etc., may be treated as more reliable than an amount of physical activity expended that is obtained by the user's manually entering his or her subjective perception of the amount of exertion that was used during an exercise session. As another example, nutrition information that is provided by a nutritional database through an application may be treated as more reliable than nutrition information obtained solely from a user's subjective impressions and estimates of food intake.

Although sensor data in many cases will be considered as more reliable than other sources of input data, the data may nevertheless be subject to a degree of uncertainty due to factors such as signal quality, calibration, connectivity and age of the sensor. For instance, in the case of a [glucose] sensor, the assigned reliability level may be reduced if the sensor signal is noisy, if the sensor has not recently been calibrated, or if the sensor is still undergoing a break-in period or has exceeded its expected lifetime. The reliability of input data from other types of sensor may be reduced for similar reasons as well.

Another factor that may impact the reliability of input data is whether the data is quantitative or qualitative. For instance, if a user manually enters nutritional information for a meal, all other things being equal, an indication of food portion size as being "small," "medium" or "large," may be treated as being less reliable than a portion size that is provided by weight in e.g., ounces or grams. That is, in some cases quantitative data may be treated as more reliable than qualitative data.

Once reliability levels have been assigned to the individual input data items that are used to generate a particular decision support recommendation, an overall reliability metric may be assigned based on the individual reliability levels. For instance, the overall reliability may be an average, weighted or unweighted, of the individual reliability levels. In some cases if an individual reliability level is deemed too low, it may be excluded from use in generating the recommendation. That is, it may be assigned a weight of zero. In some embodiments only if the overall reliability metric exceeds some threshold value will the decision support recommendation be presented to the user. In some cases, even if the overall reliability metric exceeds the threshold value, the decision support recommendation will not be presented to the user if any of the particular individual input data items have a reliability level below certain prescribed values. That is, the presentation of a recommendation may be suppressed based on an analysis of the overall reliability metric and the individual reliability levels. Of course, numerous variations in the calculation of the overall reliability metric will be understood.

The threshold value that is used to determine whether a recommendation is based on sufficiently reliable input data need not be a fixed value. Rather, in some cases it may vary depending, for instance, on the nature of the decision support recommendation. For example, a recommendation that is classified as being more conservative and safer with fewer potential risks may be presented with a lower threshold value than a recommendation that is classified as being potentially riskier. The classification of a decision support recommendation as being more or less conservative may be predetermined using any suitable guidelines. Moreover, certain types of recommendations may be inherently treated as being more conservative than other types of recommendations. For example, therapeutic recommendations in some cases may be classified as less conservative than adjunctive recommendations.

As discussed above, in some embodiments only if the overall reliability metric exceeds some threshold value will the decision support recommendation be presented to the user. In other embodiments, however, the decision support recommendation will not even be calculated unless the overall reliability metric exceeds some threshold value. In some cases, even if the overall reliability metric exceeds the threshold value, the decision support recommendation will not be calculated if any of the particular individual input data items have a reliability level below certain prescribed values. That is, the calculation of a decision support recommendation may be suppressed based on an analysis of the overall reliability metric and the individual reliability levels.

Any of a variety of mathematical frameworks may be employed to determine both the decision support recommendations and the reliability levels of the input data used to generate those recommendations, the overall reliability index, and the thresholds that are used to determine if and when a decision support recommendation is calculated or presented to the user. For example, as previously mentioned, in some cases machine-learning techniques may be employed. Such techniques can be used on population data collected from in-field use to obtain periodic, iterative improvements to the performance of the safety module. This could be particularly advantageous to identify certain sources of errors and uncertainties in reliability that occur infrequently and thus would be difficult to identify through clinical trials.

Other mathematical frameworks that may be employed include adaptive learning to learn aspects of users over time, Bayesian analysis to quantify the reliability of current input data based on prior input data, and decision fusion methods to determine the likelihood of an event occurring. In addition, heuristic techniques may be applied to the analysis framework to develop recommendations based on past experience. In the development of such heuristic solutions, related techniques may be employed such as: MPC, if/then logic, expert systems, logistic regression, neural networks, fuzzy logic, weighted functions, as well as using regression models.

In some embodiments the continuous glucose application (e.g., continuous glucose application 209 in FIG. 4) residing on the display device may periodically prompt the user to verify that the application and the display device (its hardware, software and/or firmware) are operating correctly. This is important since the display device may be user-supplied and generally will not meet medical device standards and specifications. For instance, components of the display device such as its power supply, display, enclosure and software generally will not be of medical grade. The prompts provided to the user by the application can be used as feedback to confirm that the display device is operationally intact. For instance, in some cases certain aspects of the operation of the display device may be tested by presenting the user with various screens such as a sample default trending screen, a sample warning screen, a sample decision support recommendation screen, a sample calibration screen and/or a patient record screen. The user then may be prompted to answer questions concerning the quality and accuracy of the screens and the data therein before the CGM application can be used on the display device.

What has been disclosed are systems and methods for determining decision support recommendations that can be presented to users who monitor their diabetic state to reduce their risk of complications arising from their diabetic state and to improve their metabolic control. System and methods are also disclosed for determining the reliability of the individual input data items that are used to determine a given decision support recommendation and the overall reliability of the input data items and, based on the reliability levels, to determine if the given decision support recommendation should be presented to the user. A variety of methods have been disclosed for determining the decision support recommendations and the reliability of the input data items.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, the term "message" encompasses a wide variety of formats for transmitting information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed/transmitted/stored/received/etc. in multiple parts.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray™. disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction or should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for determining a decision support recommendation for treatment of a diabetic state, the method comprising:
   identifying a current diabetic state of a user based at least in part on a glucose concentration level;
   receiving additional data that, along with the current diabetic state, are used for determining the decision support recommendation;
   assigning a separate reliability level to each of the current diabetic state and the additional data, wherein the separate reliability level assigned to the additional data is based at least in part on an identity of a source from which the additional data is obtained;
   calculating the decision support recommendation using the additional data and the current diabetic state;
   assigning an overall reliability level to the decision support recommendation based on the separate reliability levels; and
   performing the decision support recommendation to treat the diabetic state of the user based on the overall reliability level exceeding a first threshold, wherein the first threshold is selected based at least in part on a type of the decision support recommendation that is calculated, wherein performing the decision support recommendation comprises sending a command to an insulin pump, the command causing the insulin pump to automatically administer an amount of insulin.

2. The method of claim 1, wherein the additional data includes an indication of food and drink ingested or to be ingested within a prescribed period of time.

3. The method of claim 2, wherein the indication includes data manually entered by the user, nutritional data concerning the food or drink that is obtained from a third party, nutritional data automatically entered by an application, or nutritional data that is automatically entered by scanning the nutritional data into the application.

4. The method of claim 1, wherein the additional data includes information describing past physiological response patterns of the user or an indication of a user activity level that has occurred or is to occur within a prescribed amount of time.

5. The method of claim 1, wherein assigning the separate reliability level to the additional data includes assigning a higher reliability to additional information obtained through machine-to-machine communication than through manual entry-to-machine communication.

6. The method of claim 1, wherein the decision support recommendation includes a recommendation to ingest food or drink or a recommendation to inject a calculated amount of insulin.

7. The method of claim 1, wherein presenting the decision support recommendation only if the overall reliability level exceeds the first threshold further includes determining when to present the decision support recommendation based at least in part on the overall reliability level.

8. The method of claim 1, wherein receiving the additional data includes receiving a plurality of additional data items of different types and assigning the separate reliability level to the additional data includes independently assigning a separate reliability level to each of the additional data items.

9. The method of claim 8, wherein presenting the decision support recommendation includes only presenting the decision support recommendation if a weighted average of the separate reliability levels exceeds a second threshold and if none of the separate reliability levels falls below a third threshold.

10. The method of claim 1, wherein:
receiving the additional data comprises receiving a plurality of additional data items;
assigning the separate reliability level to each of the current diabetic state and the additional data comprises assigning a separate reliability level to each of the plurality of additional data items based at least in part on the identity of the source from which each of the plurality of additional data items is obtained; and
calculating the decision support recommendation comprises calculating the decision support recommendation using the plurality of additional data items and the current diabetic state.

11. The method of claim 1, wherein presenting the decision support recommendation further comprises presenting the decision support recommendation only if none of the separate reliability levels is below a second threshold.

* * * * *